United States Patent
Shalev et al.

(10) Patent No.: US 8,956,397 B2
(45) Date of Patent: Feb. 17, 2015

(54) ENDOVASCULAR FLOW DIRECTION INDICATOR

(75) Inventors: Alon Shalev, Ra'anana (IL); Sagi Raz, Tel Aviv (IL)

(73) Assignee: Endospan Ltd., Herzilyia Pituach (IL)

( * ) Notice: Subject to any disclaimer, the term of this patent is extended or adjusted under 35 U.S.C. 154(b) by 149 days.

(21) Appl. No.: 13/519,971

(22) PCT Filed: Dec. 27, 2010

(86) PCT No.: PCT/IL2010/001087
§ 371 (c)(1),
(2), (4) Date: Aug. 28, 2012

(87) PCT Pub. No.: WO2011/080738
PCT Pub. Date: Jul. 7, 2011

(65) Prior Publication Data
US 2012/0316634 A1 Dec. 13, 2012

Related U.S. Application Data

(60) Provisional application No. 61/291,427, filed on Dec. 31, 2009.

(51) Int. Cl.
| | |
|---|---|
| *A61F 2/06* | (2013.01) |
| *A61M 29/00* | (2006.01) |
| *A61F 2/95* | (2013.01) |
| *A61F 2/01* | (2006.01) |

(52) U.S. Cl.
CPC .............. *A61F 2/95* (2013.01); *A61F 2002/011* (2013.01)
USPC ......................................... 623/1.11; 606/200

(58) Field of Classification Search
USPC ......... 606/159, 200, 110–115, 191, 198, 192, 606/194, 108, 167, 170, 127, 128; 623/1.11; 604/104–109
See application file for complete search history.

(56) References Cited

U.S. PATENT DOCUMENTS

| | | | |
|---|---|---|---|
| 4,180,613 A | * | 12/1979 | Vassiliou ...................... 428/327 |
| 4,355,426 A | | 10/1982 | MacGregor |
| 4,505,767 A | | 3/1985 | Quin |
| 4,562,596 A | | 1/1986 | Kornberg |
| 4,577,631 A | | 3/1986 | Kreamer |
| 4,617,932 A | | 10/1986 | Kornberg |
| 4,665,906 A | | 5/1987 | Jervis |

(Continued)

FOREIGN PATENT DOCUMENTS

| | | |
|---|---|---|
| CA | 2 497 704 | 3/2004 |
| EP | 1 177 780 | 2/2002 |

(Continued)

OTHER PUBLICATIONS

"E-vita® open plus" product brochure (JOTEC GmbH, Hechingen, Germany), 2010.

(Continued)

*Primary Examiner* — Jocelin Tanner
(74) *Attorney, Agent, or Firm* — Sughrue Mion, PLLC

(57) ABSTRACT

An endovascular tool is provided, which includes a longitudinal delivery shaft and a fin coupled to the delivery shaft. The fin is configured to assume a compressed state for endoluminal delivery, and an expanded state for endoluminal deployment, in which state the fin is configured to pivot around an axis of rotation. Other embodiments are also described.

43 Claims, 11 Drawing Sheets

(56) References Cited

U.S. PATENT DOCUMENTS

| | | | |
|---|---|---|---|
| 4,739,762 A | 4/1988 | Palmaz | |
| 4,787,899 A | 11/1988 | Lazarus | |
| 4,878,906 A | 11/1989 | Lindemann et al. | |
| 4,886,062 A | 12/1989 | Wiktor | |
| 4,938,740 A | 7/1990 | Melbin | |
| 4,969,458 A | 11/1990 | Wiktor | |
| 5,042,707 A | 8/1991 | Taheri | |
| 5,064,435 A | 11/1991 | Porter | |
| 5,122,136 A | 6/1992 | Guglielmi et al. | |
| 5,133,732 A | 7/1992 | Wiktor | |
| 5,192,286 A * | 3/1993 | Phan et al. | 606/127 |
| 5,486,183 A | 1/1996 | Middleman et al. | |
| 5,507,769 A | 4/1996 | Marin et al. | |
| 5,509,923 A | 4/1996 | Middleman et al. | |
| 5,522,880 A | 6/1996 | Barone et al. | |
| 5,527,322 A | 6/1996 | Klein et al. | |
| 5,554,181 A | 9/1996 | Das | |
| 5,562,724 A | 10/1996 | Vorwerk et al. | |
| 5,613,974 A | 3/1997 | Andreas et al. | |
| 5,632,746 A | 5/1997 | Middleman et al. | |
| 5,632,763 A | 5/1997 | Glastra | |
| 5,632,772 A | 5/1997 | Alcime et al. | |
| 5,639,278 A | 6/1997 | Dereume et al. | |
| 5,643,340 A | 7/1997 | Nunokawa | |
| 5,653,743 A | 8/1997 | Martin | |
| 5,676,696 A | 10/1997 | Marcade | |
| 5,676,697 A | 10/1997 | McDonald | |
| 5,728,134 A | 3/1998 | Barak | |
| 5,749,879 A | 5/1998 | Middleman et al. | |
| 5,755,770 A | 5/1998 | Ravenscroft | |
| 5,755,771 A | 5/1998 | Penn et al. | |
| 5,755,777 A | 5/1998 | Chuter | |
| 5,769,882 A | 6/1998 | Fogarty et al. | |
| 5,782,903 A | 7/1998 | Wiktor | |
| 5,782,906 A | 7/1998 | Marshall et al. | |
| 5,824,040 A | 10/1998 | Cox et al. | |
| 5,860,991 A | 1/1999 | Klein et al. | |
| 5,876,432 A | 3/1999 | Lau et al. | |
| 5,906,641 A | 5/1999 | Thompson et al. | |
| 5,921,994 A | 7/1999 | Andreas et al. | |
| 6,015,431 A | 1/2000 | Thornton et al. | |
| 6,033,435 A | 3/2000 | Penn et al. | |
| 6,059,824 A | 5/2000 | Taheri | |
| 6,099,497 A | 8/2000 | Adams et al. | |
| 6,117,145 A | 9/2000 | Wood et al. | |
| 6,200,339 B1 | 3/2001 | Leschinsky et al. | |
| 6,206,893 B1 | 3/2001 | Klein et al. | |
| 6,270,524 B1 | 8/2001 | Kim | |
| 6,283,991 B1 | 9/2001 | Cox et al. | |
| 6,290,720 B1 | 9/2001 | Khosravi et al. | |
| 6,325,823 B1 | 12/2001 | Horzewski et al. | |
| 6,428,565 B1 | 8/2002 | Wisselink | |
| 6,471,722 B1 | 10/2002 | Inoue | |
| 6,506,211 B1 | 1/2003 | Skubitz et al. | |
| 6,544,279 B1 * | 4/2003 | Hopkins et al. | 606/200 |
| 6,613,078 B1 | 9/2003 | Barone | |
| 6,635,083 B1 | 10/2003 | Cheng et al. | |
| 6,652,567 B1 | 11/2003 | Deaton | |
| 6,656,214 B1 | 12/2003 | Fogarty et al. | |
| 6,673,080 B2 * | 1/2004 | Reynolds et al. | 606/127 |
| 6,692,520 B1 | 2/2004 | Gambale et al. | |
| 6,695,833 B1 | 2/2004 | Frantzen | |
| 6,743,195 B2 | 6/2004 | Zucker | |
| 6,776,794 B1 | 8/2004 | Hong et al. | |
| 6,814,749 B2 | 11/2004 | Cox et al. | |
| 6,814,752 B1 | 11/2004 | Chuter | |
| 6,824,560 B2 | 11/2004 | Pelton | |
| 6,846,321 B2 | 1/2005 | Zucker | |
| 6,907,285 B2 | 6/2005 | Denker et al. | |
| 6,908,477 B2 | 6/2005 | McGuckin, Jr. et al. | |
| 6,929,660 B1 | 8/2005 | Ainsworth et al. | |
| 6,942,691 B1 | 9/2005 | Chuter | |
| 6,964,679 B1 | 11/2005 | Marcade et al. | |
| 6,986,774 B2 | 1/2006 | Middleman et al. | |
| 7,008,441 B2 | 3/2006 | Zucker | |
| 7,044,962 B2 | 5/2006 | Elliott | |
| 7,105,020 B2 | 9/2006 | Greenberg et al. | |
| 7,112,217 B1 | 9/2006 | Kugler et al. | |
| 7,115,127 B2 | 10/2006 | Lindenbaum et al. | |
| 7,144,421 B2 | 12/2006 | Carpenter et al. | |
| 7,201,772 B2 | 4/2007 | Schwammenthal et al. | |
| 7,223,266 B2 | 5/2007 | Lindenbaum et al. | |
| 7,279,003 B2 | 10/2007 | Berra et al. | |
| 7,306,623 B2 | 12/2007 | Watson | |
| 7,341,598 B2 | 3/2008 | Davidson et al. | |
| 7,407,509 B2 | 8/2008 | Greenberg et al. | |
| 7,429,269 B2 | 9/2008 | Schwammenthal et al. | |
| 7,442,204 B2 | 10/2008 | Schwammenthal et al. | |
| 7,473,272 B2 | 1/2009 | Pryor | |
| 7,537,609 B2 | 5/2009 | Davidson et al. | |
| 7,540,881 B2 | 6/2009 | Meyer et al. | |
| 7,544,160 B2 | 6/2009 | Gross | |
| 7,637,939 B2 | 12/2009 | Tischler | |
| 7,662,161 B2 | 2/2010 | Briganti et al. | |
| 7,662,168 B2 | 2/2010 | McGuckin, Jr. et al. | |
| 7,678,141 B2 | 3/2010 | Greenan et al. | |
| 7,722,626 B2 | 5/2010 | Middleman et al. | |
| 7,731,732 B2 | 6/2010 | Ken | |
| 7,815,673 B2 | 10/2010 | Bloom et al. | |
| 7,959,662 B2 | 6/2011 | Erbel et al. | |
| 2001/0014823 A1 | 8/2001 | Ressemann et al. | |
| 2001/0044652 A1 | 11/2001 | Moore | |
| 2001/0053930 A1 | 12/2001 | Kugler et al. | |
| 2002/0099441 A1 | 7/2002 | Dehdashtian | |
| 2002/0123791 A1 | 9/2002 | Harrison | |
| 2002/0156495 A1 | 10/2002 | Brenneman et al. | |
| 2002/0183783 A1 * | 12/2002 | Shadduck | 606/200 |
| 2002/0198585 A1 | 12/2002 | Wisselink | |
| 2003/0093145 A1 | 5/2003 | Lawrence-Brown et al. | |
| 2003/0130720 A1 | 7/2003 | DePalma et al. | |
| 2003/0153944 A1 * | 8/2003 | Phung et al. | 606/200 |
| 2003/0153968 A1 | 8/2003 | Geis et al. | |
| 2003/0171771 A1 * | 9/2003 | Anderson et al. | 606/200 |
| 2003/0199967 A1 | 10/2003 | Hartley et al. | |
| 2003/0212449 A1 | 11/2003 | Cox | |
| 2003/0233117 A1 * | 12/2003 | Adams et al. | 606/200 |
| 2003/0236567 A1 | 12/2003 | Elliot | |
| 2004/0015227 A1 | 1/2004 | Vardi et al. | |
| 2004/0106972 A1 | 6/2004 | Deaton | |
| 2004/0106978 A1 | 6/2004 | Greenberg et al. | |
| 2004/0133266 A1 | 7/2004 | Clerc et al. | |
| 2004/0171978 A1 | 9/2004 | Shalaby | |
| 2004/0181149 A1 | 9/2004 | Langlotz et al. | |
| 2004/0215327 A1 | 10/2004 | Doig et al. | |
| 2005/0010246 A1 * | 1/2005 | Streeter et al. | 606/200 |
| 2005/0033406 A1 | 2/2005 | Barnhart et al. | |
| 2005/0049678 A1 | 3/2005 | Cocks et al. | |
| 2005/0065545 A1 | 3/2005 | Wallace | |
| 2005/0102018 A1 | 5/2005 | Carpenter et al. | |
| 2005/0102021 A1 | 5/2005 | Osborne | |
| 2005/0131517 A1 | 6/2005 | Hartley et al. | |
| 2005/0149166 A1 | 7/2005 | Schaeffer et al. | |
| 2005/0171598 A1 | 8/2005 | Schaeffer et al. | |
| 2005/0203606 A1 | 9/2005 | VanCamp | |
| 2005/0222668 A1 | 10/2005 | Schaeffer et al. | |
| 2005/0222669 A1 | 10/2005 | Purdy | |
| 2006/0015170 A1 | 1/2006 | Jones et al. | |
| 2006/0052799 A1 | 3/2006 | Middleman et al. | |
| 2006/0069426 A1 | 3/2006 | Weinberger | |
| 2006/0100684 A1 | 5/2006 | Elliott | |
| 2006/0149360 A1 | 7/2006 | Schwammenthal et al. | |
| 2006/0155358 A1 | 7/2006 | LaDuca et al. | |
| 2006/0155366 A1 | 7/2006 | LaDuca et al. | |
| 2006/0167476 A1 | 7/2006 | Burdulis, Jr. et al. | |
| 2006/0193892 A1 | 8/2006 | Furst et al. | |
| 2006/0229709 A1 | 10/2006 | Morris et al. | |
| 2006/0241740 A1 | 10/2006 | Vardi et al. | |
| 2006/0281966 A1 | 12/2006 | Peacock, III | |
| 2007/0021822 A1 | 1/2007 | Boatman | |
| 2007/0043425 A1 | 2/2007 | Hartley et al. | |
| 2007/0055350 A1 | 3/2007 | Erickson et al. | |
| 2007/0055358 A1 | 3/2007 | Krolik et al. | |
| 2007/0060989 A1 | 3/2007 | Deem et al. | |
| 2007/0073373 A1 | 3/2007 | Bonsignore | |

(56) References Cited

U.S. PATENT DOCUMENTS

| | | |
|---|---|---|
| 2007/0088425 A1 | 4/2007 | Schaeffer |
| 2007/0112344 A1 | 5/2007 | Keilman |
| 2007/0135677 A1 | 6/2007 | Miller et al. |
| 2007/0142896 A1 | 6/2007 | Anderson et al. |
| 2007/0150051 A1 | 6/2007 | Arnault de la et al. |
| 2007/0156167 A1 | 7/2007 | Connors et al. |
| 2007/0167898 A1 | 7/2007 | Peters et al. |
| 2007/0185565 A1 | 8/2007 | Schwammenthal et al. |
| 2007/0208410 A1 | 9/2007 | Berra et al. |
| 2007/0213805 A1 | 9/2007 | Schaeffer et al. |
| 2007/0219610 A1 | 9/2007 | Israel |
| 2007/0233229 A1 | 10/2007 | Berra et al. |
| 2007/0237973 A1 | 10/2007 | Purdy et al. |
| 2007/0244542 A1 | 10/2007 | Greenan et al. |
| 2007/0244543 A1 | 10/2007 | Mitchell |
| 2007/0244547 A1 | 10/2007 | Greenan |
| 2007/0255388 A1 | 11/2007 | Rudakov et al. |
| 2008/0002871 A1 | 1/2008 | Gunzert-Marx et al. |
| 2008/0015673 A1 | 1/2008 | Chuter |
| 2008/0058918 A1 | 3/2008 | Watson |
| 2008/0109066 A1 | 5/2008 | Quinn |
| 2008/0114445 A1 | 5/2008 | Melsheimer et al. |
| 2008/0147173 A1 | 6/2008 | McIff et al. |
| 2008/0167704 A1 | 7/2008 | Wright et al. |
| 2008/0269789 A1 | 10/2008 | Eli |
| 2008/0275540 A1 | 11/2008 | Wen |
| 2008/0275542 A1 | 11/2008 | LaDuca et al. |
| 2008/0288044 A1 | 11/2008 | Osborne |
| 2008/0319528 A1 | 12/2008 | Yribarren et al. |
| 2009/0012597 A1 | 1/2009 | Doig et al. |
| 2009/0012602 A1 | 1/2009 | Quadri |
| 2009/0030502 A1 | 1/2009 | Sun et al. |
| 2009/0048663 A1 | 2/2009 | Greenberg |
| 2009/0082847 A1 | 3/2009 | Zacharias |
| 2009/0099648 A1 | 4/2009 | Yu |
| 2009/0099649 A1 | 4/2009 | Chobotov et al. |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1 | 5/2009 | Pinchuk et al. |
| 2009/0149877 A1 | 6/2009 | Hanson et al. |
| 2009/0240316 A1 | 9/2009 | Bruszewski |
| 2009/0248134 A1 | 10/2009 | Dierking et al. |
| 2009/0254170 A1 | 10/2009 | Hartley et al. |
| 2009/0259290 A1 | 10/2009 | Bruszewski et al. |
| 2009/0287145 A1 | 11/2009 | Cragg et al. |
| 2010/0063575 A1 | 3/2010 | Shalev |
| 2010/0070019 A1 | 3/2010 | Shalev |
| 2010/0161026 A1 | 6/2010 | Brocker et al. |
| 2011/0093002 A1 | 4/2011 | Rucker et al. |
| 2011/0208289 A1 | 8/2011 | Shalev |
| 2011/0208296 A1 | 8/2011 | Duffy et al. |
| 2011/0208297 A1 | 8/2011 | Tuval et al. |
| 2011/0208298 A1 | 8/2011 | Tuval et al. |
| 2011/0218607 A1 | 9/2011 | Arbefeuille et al. |
| 2011/0264184 A1 | 10/2011 | Heltai |
| 2011/0288622 A1 | 11/2011 | Chan et al. |

FOREIGN PATENT DOCUMENTS

| | | |
|---|---|---|
| EP | 1 325 716 | 7/2003 |
| JP | 2002-253682 | 9/2002 |
| WO | 2004/017868 | 3/2004 |
| WO | 2005/002466 | 1/2005 |
| WO | 2005/037138 | 4/2005 |
| WO | 2005/041781 | 5/2005 |
| WO | 2005/041783 | 5/2005 |
| WO | 2006/007389 | 1/2006 |
| WO | 2006/028925 | 3/2006 |
| WO | 2006/070372 | 7/2006 |
| WO | 2007/022495 | 2/2007 |
| WO | 2007/084547 | 7/2007 |
| WO | 2007/144782 | 12/2007 |
| WO | 2008/008291 | 1/2008 |
| WO | 2008/035337 | 3/2008 |
| WO | 2008/042266 | 4/2008 |
| WO | 2008/047092 | 4/2008 |
| WO | 2008/047354 | 4/2008 |
| WO | 2008/053469 | 5/2008 |
| WO | 2008/107885 | 9/2008 |
| WO | 2008/140796 | 11/2008 |
| WO | 2009/078010 | 6/2009 |
| WO | 2009/116041 | 9/2009 |
| WO | 2009/116042 | 9/2009 |
| WO | 2009/118733 | 10/2009 |
| WO | 2010/024869 | 3/2010 |
| WO | 2010/024879 | 3/2010 |
| WO | 2010/031060 | 3/2010 |
| WO | 2010/045238 | 4/2010 |
| WO | 2010/062355 | 6/2010 |
| WO | 2010/088776 | 8/2010 |
| WO | 2010/128162 | 11/2010 |
| WO | 2010/150208 | 12/2010 |
| WO | 2011/004374 | 1/2011 |
| WO | 2011/007354 | 1/2011 |
| WO | 2011/055364 | 5/2011 |
| WO | 2011/064782 | 6/2011 |
| WO | 2011/067764 | 6/2011 |
| WO | 2011/070576 | 6/2011 |
| WO | 2011/080738 | 7/2011 |
| WO | 2011/095979 | 8/2011 |
| WO | 2011/106532 | 9/2011 |
| WO | 2011/106533 | 9/2011 |
| WO | 2011/106544 | 9/2011 |

OTHER PUBLICATIONS

Fonseca A et al., "Intravascular ultrasound assessment of the novel AngioSculpt scoring balloon catheter for the treatment of complex coronary lesions," J Invasive Cardiol 20(1):21-7 (Jan. 2008).

Khlif H et al., "Contribution to the Improvement of Textile Vascular Prostheses Crimping," Trends in Applied Sciences Research 6(9):1019-1027 (2011).

An International Search Report dated Feb. 18, 2010, which issued during the prosecution of Applicant's PCT/IL08/000287.

A Written Opinion dated Nov. 12, 2009, which issued during the prosecution of Applicant's PCT/IL08/000287.

An International Search Report dated Apr. 28, 2011, which issued during the prosecution of Applicant's PCT/IB2010/052861.

A Written Opinion dated Dec. 23, 2011, which issued during the prosecution of Applicant's PCT/IB2010/052861.

An International Search Report dated Dec. 3, 2010, which issued during the prosecution of Applicant's PCT/IL2010/000564.

A Written Opinion dated Jan. 14, 2012, which issued during the prosecution of Applicant's PCT/IL2010/000564.

An International Search Report dated Nov. 5, 2010, which issued during the prosecution of Applicant's PCT/IL2010/000549.

A Written Opinion dated Jan. 9, 2012, which issued during the prosecution of Applicant's PCT/IL2010/000549.

An International Search Report dated Oct. 6, 2011, which issued during the prosecution of Applicant's PCT/IL2010/000999.

An International Search Report dated Mar. 10, 2011, which issued during the prosecution of Applicant's PCT/IL2010/000917.

An International Search Report dated Jun. 9, 2011, which issued during the prosecution of Applicant's PCT/IL2010/001018.

An International Search Report dated Jun. 16, 2011, which issued during the prosecution of Applicant's PCT/IL2010/001037.

An International Search Report dated Jul. 7, 2011, which issued during the prosecution of Applicant's PCT/IL2010/001087.

An International Search Report dated Aug. 11, 2011, which issued during the prosecution of Applicant's PCT/IL2011/000135.

An International Search Report dated Mar. 11, 2010, which issued during the prosecution of Applicant's PCT/IL2008/001621.

A Written Opinion dated Jun. 15, 2010, which issued during the prosecution of Applicant's PCT/IL2008/001621.

An International Search Report dated Sep. 3, 2009, which issued during the prosecution of Applicant's PCT/IL2007/001312.

A Written Opinion dated Jul. 31, 2009, which issued during the prosecution of Applicant's PCT/IL2007/001312.

(56) References Cited

OTHER PUBLICATIONS

An English translation of an Office Action dated Aug. 25, 2011, which issued during the prosecution of Chinese Patent Application No. 200880014919.9.

An Office Action dated Nov. 12, 2010, which issued during the prosecution of U.S. Appl. No. 12/447,684.

An Office Action dated Apr. 27, 2011, which issued during the prosecution of U.S. Appl. No. 12/447,684.

An International Search Report together with Written Opinion both dated May 23, 2011, which issued during the prosecution of Applicant's PCT/IL10/01087.

An International Search Report together with Written Opinion both dated Jun. 14, 2013, which issued during the prosecution of Applicant's PCT/IL2012/050506.

Van Prehn J et al.: "Oversizing of aortic stent grafts for abdominal aneurysm repair: a systematic review of the benefits and risks", Eur J. Vasc Endovasc Surg., Jul. 2009;38(1):42-53. Epub May 9, 2009.

Rossella Fattori et al.: "Degenerative aneurysm of the descending aorta. Endovascular treatment", Multimedia Manual of Cardiothoracic Surgery / doi:10.1510/mmcts.2007.002824 (2007).

Office Action issued on Oct. 27, 2014 in Canadian Patent Application No. 2,785,953.

* cited by examiner

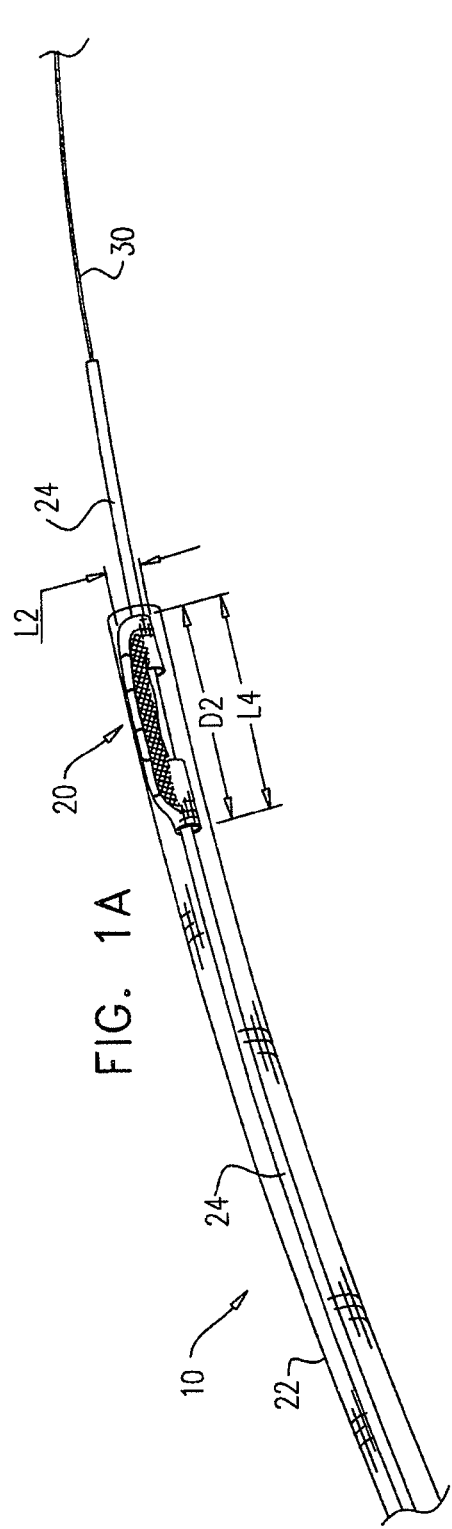
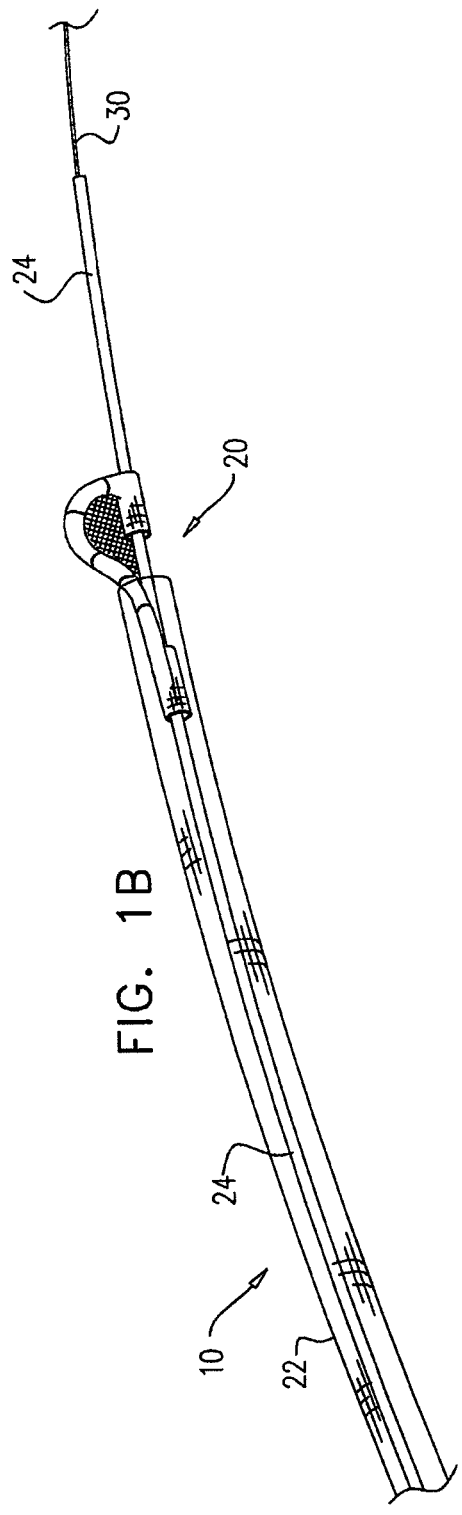

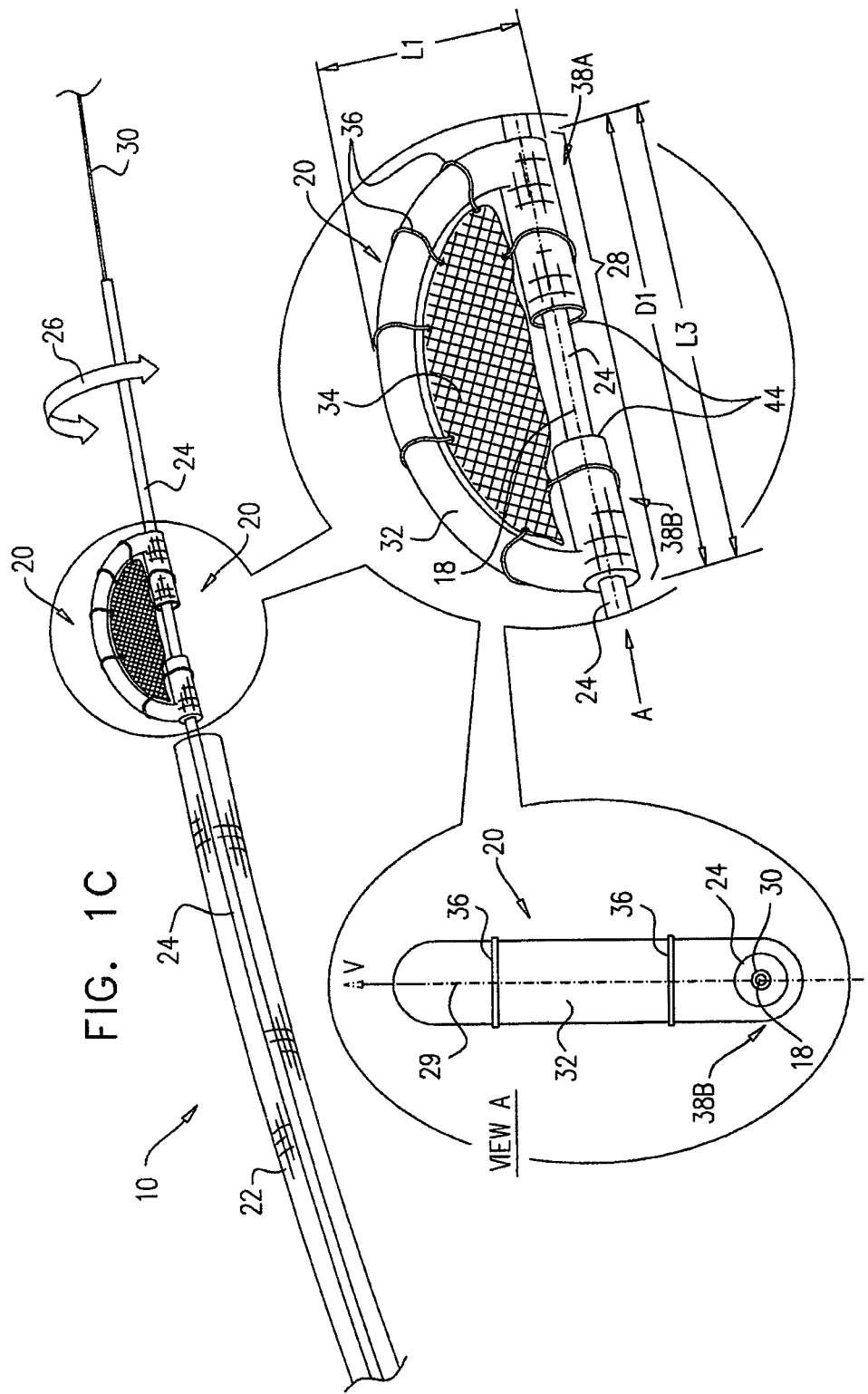

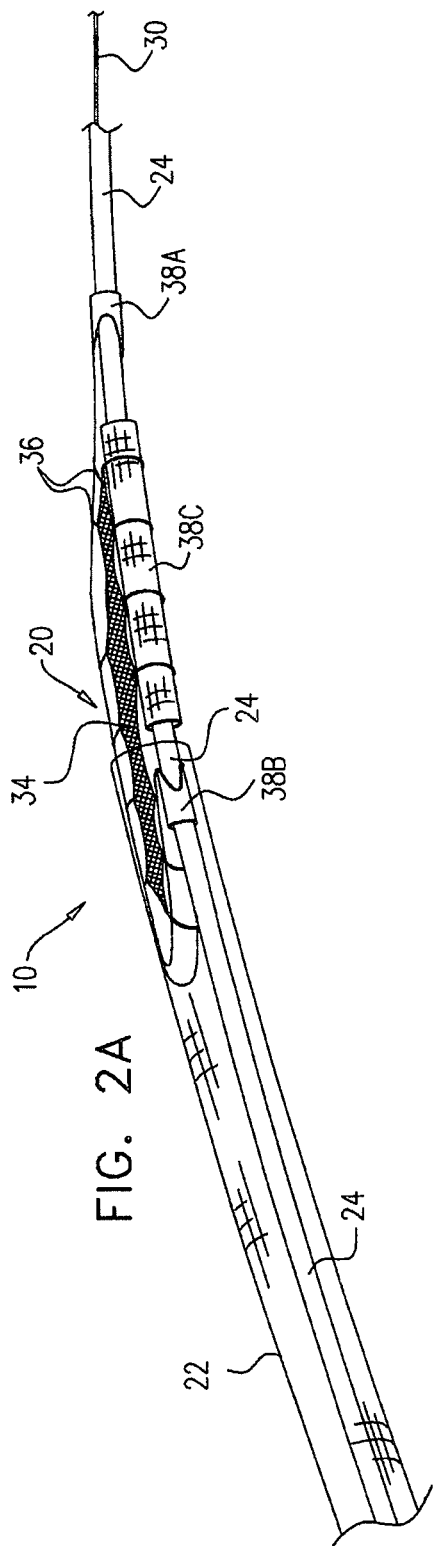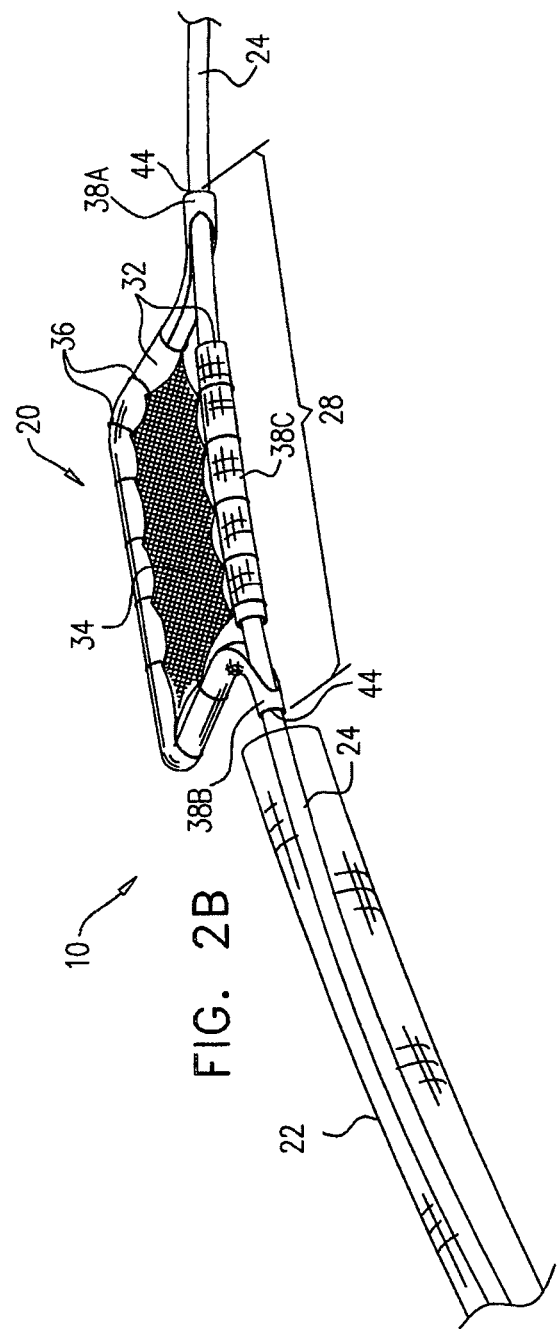

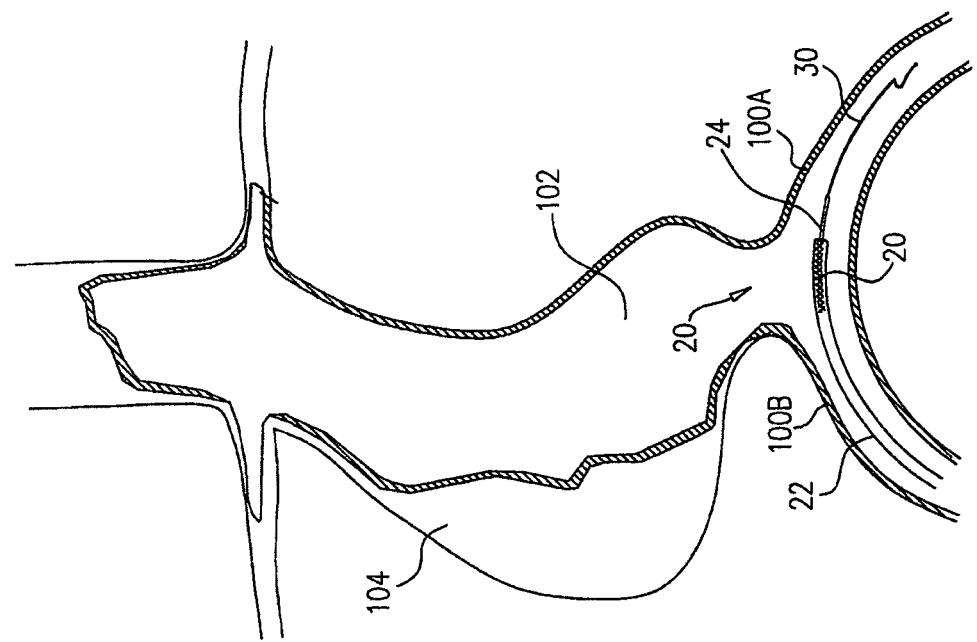
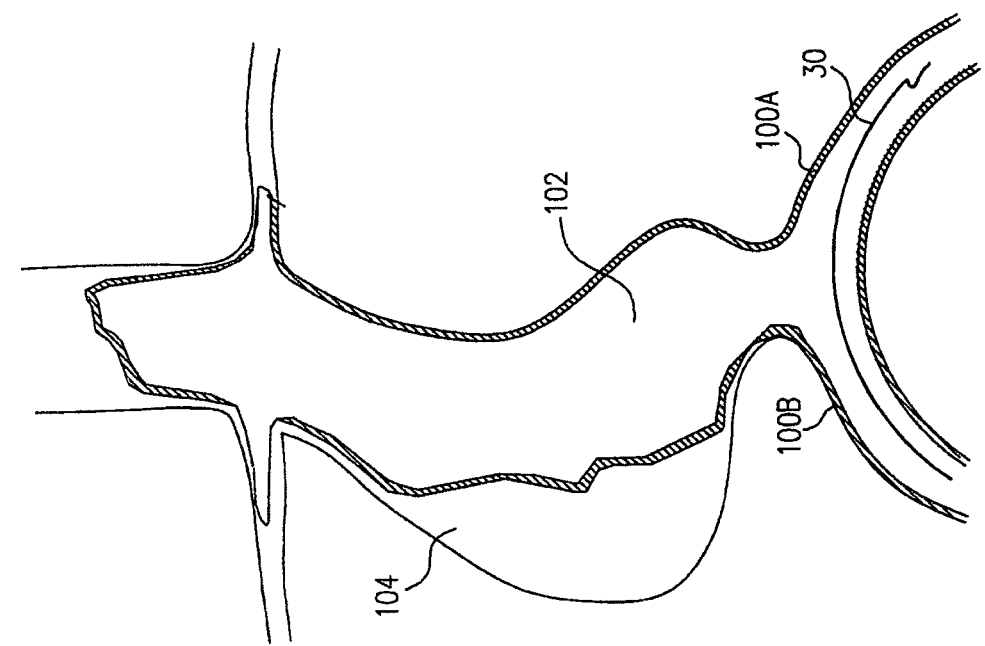

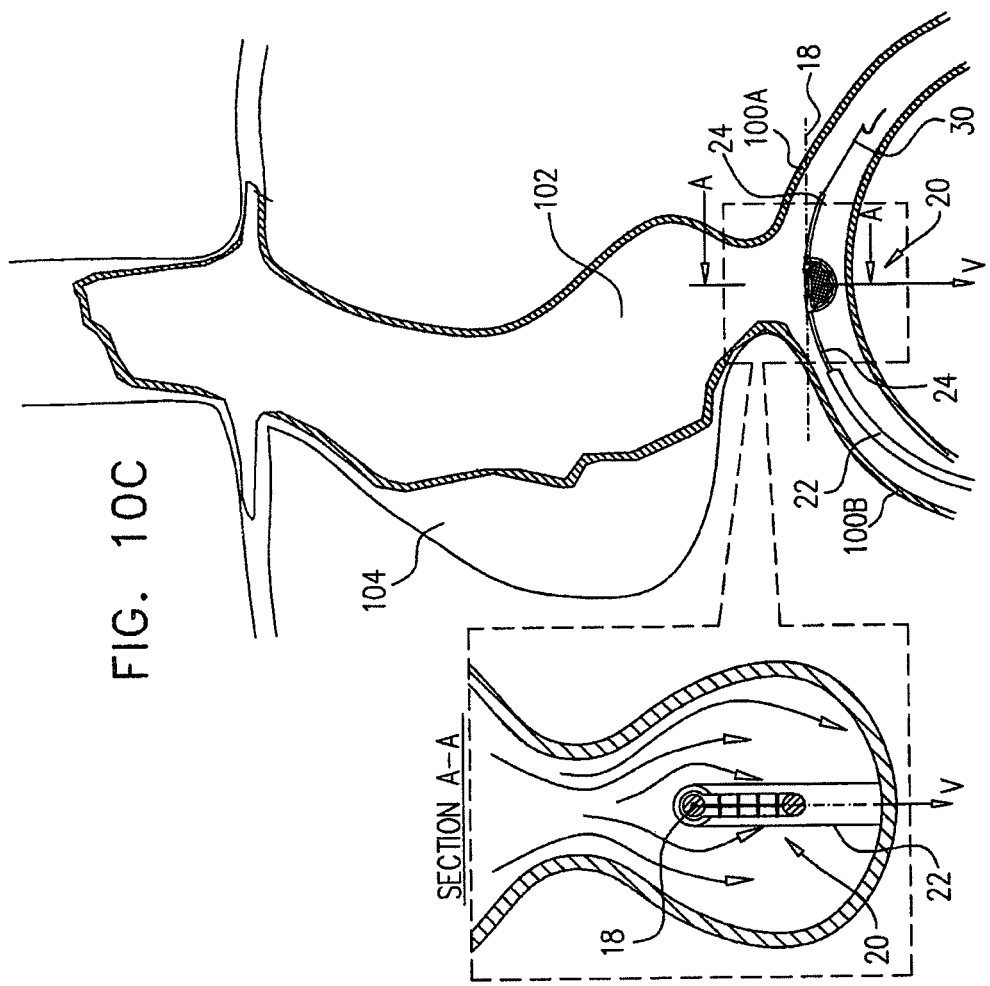

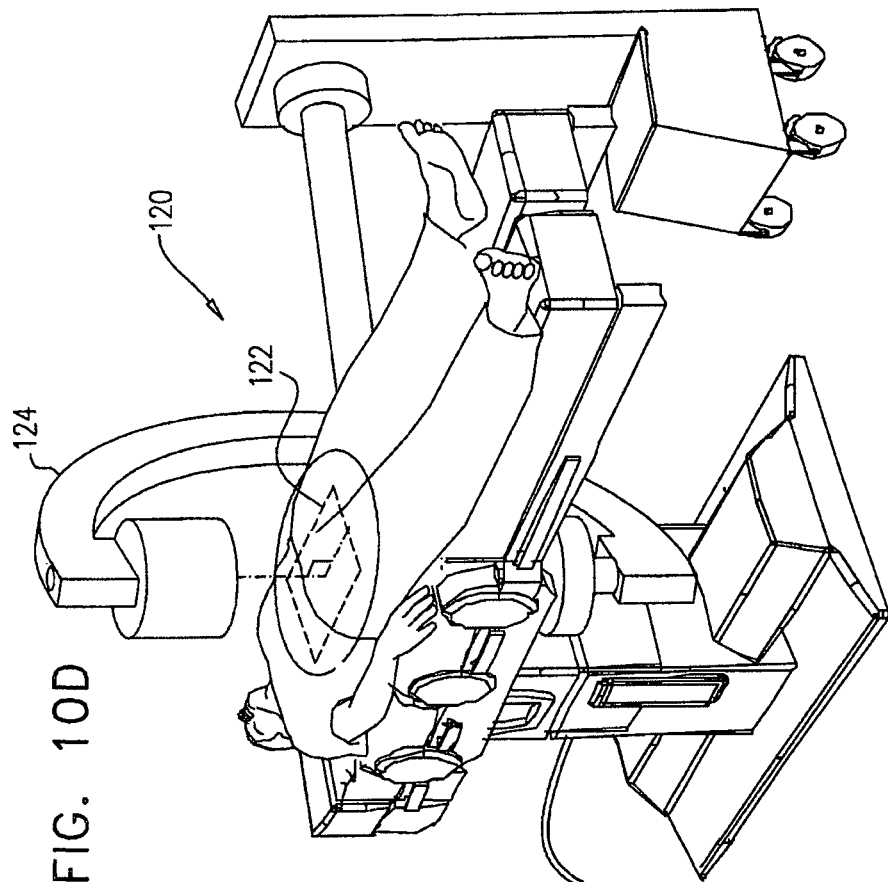
FIG. 10D
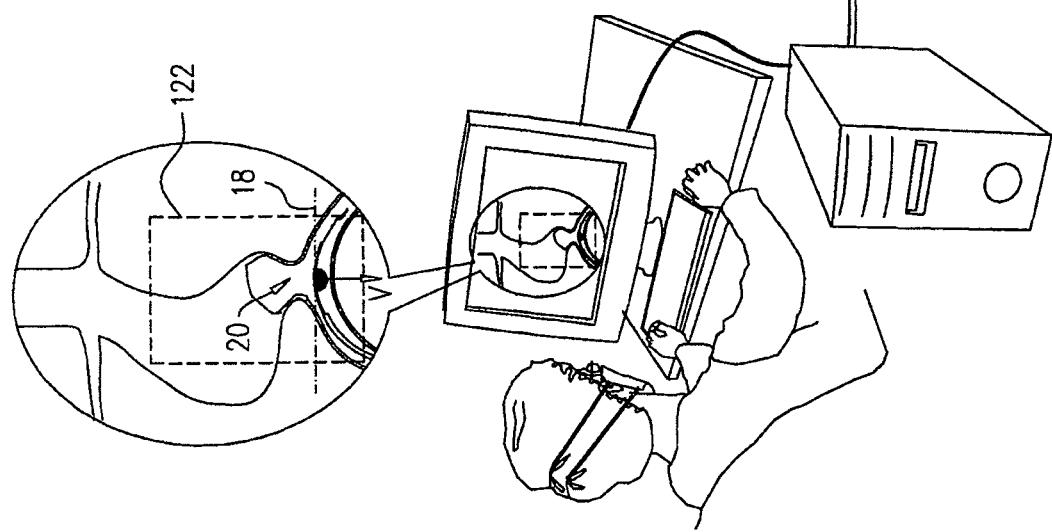

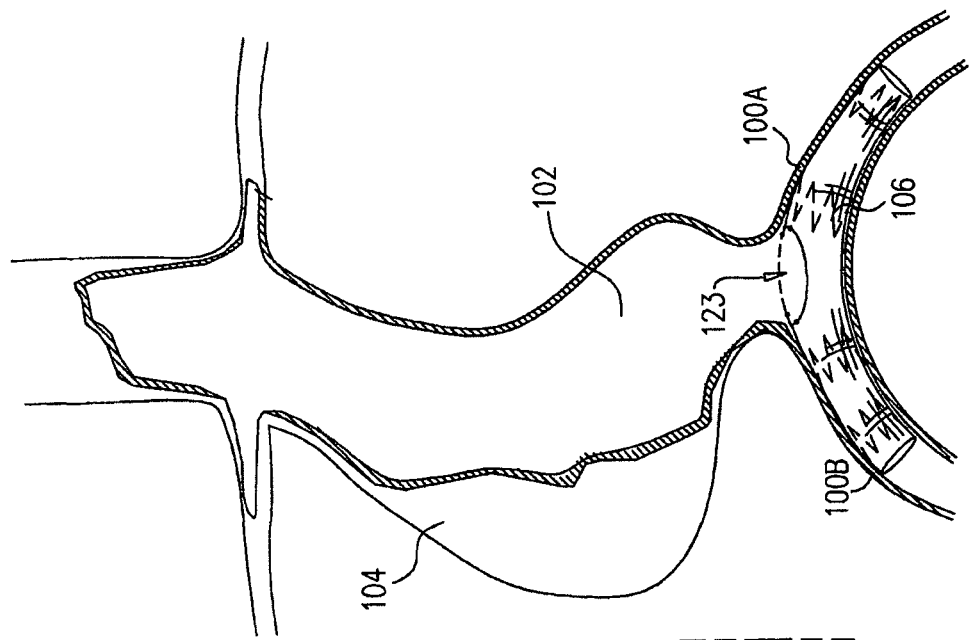
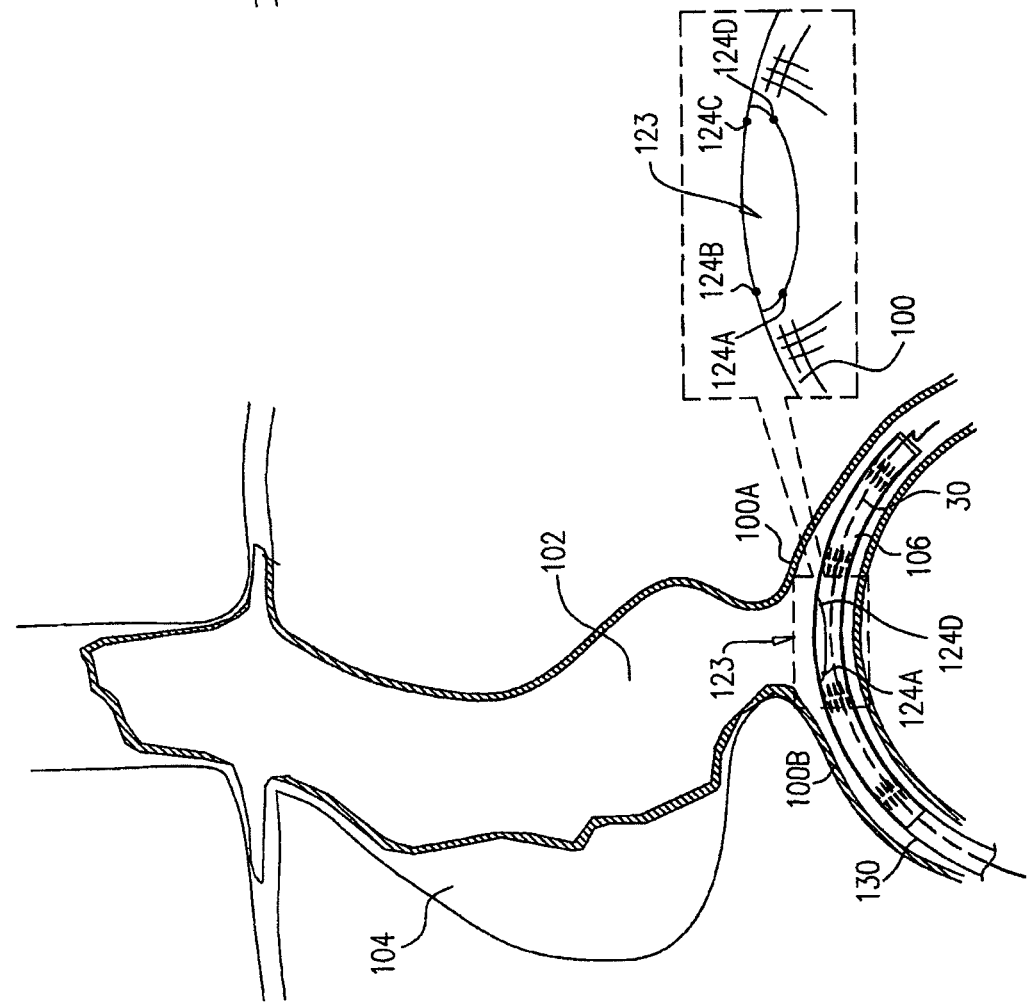

ENDOVASCULAR FLOW DIRECTION INDICATOR

CROSS-REFERENCE TO RELATED APPLICATIONS

The present patent application is the U.S. national stage of International Application PCT/IL2010/001087, filed Dec. 27, 2010, which claims priority from US Provisional Application 61/291,427, filed Dec. 31, 2009, entitled, "Endovascular flow direction indicator and methods for using such," which is incorporated herein by reference.

FIELD OF THE APPLICATION

This present application relates generally to surgical tools and methods, and specifically to endovascular surgical tools and techniques for implanting prostheses to maintain patency of body passages such as blood vessels, such as for treating aneurysms.

BACKGROUND OF THE APPLICATION

Endovascular prostheses are sometimes used to treat aortic aneurysms. Such treatment includes implanting a stent or stent-graft within the diseased vessel to bypass the anomaly. An aneurysm is a sac formed by the dilation of the wall of the artery. Aneurysms may be congenital, but are usually caused by disease or, occasionally, by trauma. Aortic aneurysms which commonly form between the renal arteries and the iliac arteries are referred to as abdominal aortic aneurysms ("AAAs"). Other aneurysms occur in the aorta, such as thoracic aortic aneurysms ("TAAs") and aortic uni-iliac ("AUI") aneurysms.

PCT Publication WO 2008/107885 to Shalev et al., and US Patent Application Publication 2010/0063575 to Shalev et al. in the US national stage thereof, which are incorporated herein by reference, describe a multiple-component expandable endoluminal system for treating a lesion at a bifurcation, including a self expandable tubular root member having a side-looking engagement aperture, and a self expandable tubular trunk member comprising a substantially blood impervious polymeric liner secured therealong. Both have a radially-compressed state adapted for percutaneous intraluminal delivery and a radially-expanded state adapted for endoluminal support.

The following references may be of interest:
U.S. Pat. No. 4,938,740 to Melbin
U.S. Pat. No. 5,824,040 to Cox et al.
U.S. Pat. No. 7,044,962 to Elliott
U.S. Pat. No. 7,544,160 to Gross
US Patent Application Publication 2006/0229709 to Morris et al.
US Patent Application Publication 2006/0241740 to Vardi et al.
US Patent Application Publication 2008/0109066 to Quinn
PCT Publication WO 09/118,733 to Karasik
PCT Publication WO 10/031,060 to Tuval et al.

SUMMARY OF APPLICATIONS

Some applications of the present invention provide an endovascular tool useful for aligning an imaging system, in order to facilitate properly aligning an implantable medical device, such as a vascular stent. The endovascular tool comprises a longitudinal delivery shaft and a fin coupled to the delivery shaft. The fin is configured to assume a compressed state for endoluminal delivery, and an expanded state for endoluminal deployment, in which state the fin is configured to pivot around an axis of rotation. The fin is configured such that, when the fin is placed in a blood flow path, at least a portion of the fin pivots in a direction that is indicative of a direction of blood flow in a vicinity of the fin.

For some applications, the fin is endoluminally deployed in one or more blood vessels of a subject, such as in the left and right common iliac arteries in a vicinity of a bifurcation with the descending abdominal aorta. The endovascular tool is endoluminally introduced into the one or more blood vessels while the fin is in its compressed state, typically in an outer shaft. The outer shaft is withdrawn proximally, thereby delivering the fin from the outer shaft, and transitioning the fin to its expanded state.

In its expanded state, the fin is configured to pivot around the axis of rotation, as described above. When the fin is thus placed in a blood flow path (such as blood flow downstream from the descending abdominal aorta into the iliac arteries), at least a portion of the fin pivots in a direction that is indicative of the direction of blood flow in the vicinity of the fin. The tool is positioned such that the axis of rotation is generally perpendicular to the direction of blood flow in the vicinity of the axis of rotation.

A radiographic image (such as a fluoroscopy image) of the fin is generated using an imaging system. The image is used to align an image plane of the imaging system generally parallel to a plane defined by the fin that is indicative of the direction of blood flow in the vicinity of the fin. This plane is defined by (a) the axis of rotation of the fin and (b) a vector oriented in the direction that the fin extends from the axis of rotation.

In order to align the image plane of the imaging system, a spatial attitude of a component of the imaging system (such as a C-arm) is changed (sometimes repeatedly), responsively to the radiographic image, until the image plane is generally parallel to the plane indicative of the direction of the blood flow in the vicinity of the fin.

For some applications, in order to align the image plane, after generating the image, one or more apparent dimensions of the fin as shown in the image are assessed, and the spatial attitude of the component of the imaging system is changed responsively to the assessing. In general, the fin will appear with a modified aspect ratio in the image to the extent that the image plane is not parallel with the plane indicative of the direction of blood flow in the vicinity of the fin. The spatial attitude of the component of the imaging system is adjusted until the fin appears to have its actual aspect ratio, indicating that the image plane and plane indicative of the direction of blood flow in the vicinity of the fin are parallel. In other words, the spatial attitude of the component of the imaging system is adjusted until an apparent shape of the fin (either of the entire fin, or of a portion thereof, such as one or more radiographic markers thereof), as shown in the radiographic image, is no longer distorted (e.g., no longer has a modified aspect ratio) compared to an actual shape of the fin, (e.g., appears to have its actual aspect ratio). Typically, the assessing and changing of the spatial attitude are repeated until a desired relationship has been obtained between the apparent dimensions and the actual dimensions of the fin.

After the imaging system has been properly aligned, the delivery shaft and the fin are withdrawn from the patient. Typically, the fin is first transitioned back to its compressed state, by retracting the fin into the outer shaft, by either advancing the outer shaft distally, and/or withdrawing the delivery shaft proximally.

A medical device, such as a stent (which, optionally, comprises a stent-graft), is introduced into vasculature of the subject, typically the one or more blood vessels from which the fin was withdrawn, or one or more other blood vessels in a vicinity of the one or more blood vessels from which the fin was withdrawn. The medical device is oriented using one or more images generated by the imaging system. Because the imaging system is properly aligned, as described above, the medical device can be properly aligned using images generated by the imaging system.

For some applications, the medical device, e.g., the stent, is rotationally oriented using the one or more images generated by the imaging system. For example, the stent may be shaped so as to define a lateral opening, and the lateral opening may be rotationally oriented using the imaging system, such as to face in a direction that is parallel to the image plane. If the imaging plane of the imaging system were not properly aligned as described above, the lateral opening would not be properly rotated to face the descending abdominal aorta, but instead would face another direction parallel to the misaligned imaging plane. Without the use of the alignment technique described herein, the imaging plane is sometimes misaligned with the plane indicative of the direction of blood flow by up to about 20 degrees, which results in the lateral opening being misaligned with the bifurcation with the descending abdominal aorta by up to about 20 degrees.

For some applications, the fin comprises a structural member and at least one substantially flow-resistant membrane member, which is securely mounted to at least a portion of the structural member. Typically, the fin is at least partially radiopaque, in order to facilitate radiographic imaging of the fin.

For some applications, the fin extends laterally from a portion of the delivery shaft, and a longitudinal axis of the portion coincides with the axis of rotation of the fin.

For some applications, the fin is shaped so as to define one or more pivot joints, which rotatably couple the fin to the portion of the delivery shaft. Typically, the pivot joints are configured to facilitate at least 180 degrees of rotation of the fin around the delivery shaft, at least when the fin is in its expanded state. Typically, the pivot joints and the delivery shaft are configured to facilitate low-friction rotation of the fin around the delivery shaft, at least when the fin is in its expanded state.

For some applications, the fin has a substantially planar shape when in its expanded state. For example, the substantially planar shape may be a parallelogram, a rectangle, a square, a semicircle, a trapezoid, a shape defined by a curved segment having ends connected by a straight line, or a shape defined by an arc having ends connected by a straight line.

For some applications, the endovascular tool is used to treat an aneurysm, such as an aortic aneurysm, or an aneurism of another blood vessel. For example, the aneurism may be of the sub-renal aorta.

There is therefore provided, in accordance with an application of the present invention, apparatus including an endovascular tool, which includes:

a longitudinal delivery shaft; and a fin, which is coupled to the delivery shaft, and which is configured to assume (a) a compressed state for endoluminal delivery, and (b) an expanded state for endoluminal deployment, in which state the fin is configured to pivot around an axis of rotation.

Typically, the fin is configured such that, when the fin is placed in a blood flow path, at least a portion of the fin pivots in a direction that is indicative of a direction of blood flow in a vicinity of the fin.

For some applications, the fin is pivotable to rotate at least 180 degrees around the axis of rotation, at least when the fin is in its expanded state.

For some applications, the delivery shaft has a length of at least 10 cm.

For some applications, the fin, at least when in its expanded state, extends laterally from a portion of the delivery shaft, and a longitudinal axis of the portion coincides with the axis of rotation. For some applications, the longitudinal axis of the portion of the delivery shaft substantially lies within a plane generally defined by the fin when in its expanded state. For some applications, the fin includes a structural member and a substantially flow-resistant membrane member, which is securely mounted to at least a portion of the structural member, and the longitudinal axis of the portion of the delivery shaft substantially lies within a plane generally defined by the membrane member when the fin is in its expanded state.

For some applications, the fin is shaped so as to define one or more pivot joints, which rotatably couple the fin to the portion of the delivery shaft. For some applications, each of the one or more pivot joints is shaped so as to surround at least 210 degrees of the delivery shaft. For some applications, the pivot joints are configured to facilitate at least 180 degrees of rotation of the fin around the delivery shaft, at least when the fin is in its expanded state. For some applications, the pivot joints and the delivery shaft are configured to facilitate low-friction rotation of the fin around the delivery shaft, at least when the fin is in its expanded state. For some applications, the pivot joints and the delivery shaft are configured to provide a coefficient of static friction between the pivot joints and the delivery shaft of no more than 0.5. For some applications, the pivot joints and the delivery shaft are configured such that the pivot joints rotate with respect to the delivery shaft even when the fin is positioned in a blood flow of a healthy peripheral artery having a diameter of at least 3 mm in a subject having a systolic to diastolic blood pressure gradient of at least 30 mmHg. For some applications, at least one of the pivot joints (e.g., exactly one of the pivot joints, or two or more of the pivot joints) is axially fixed to the delivery shaft so as to prevent axial motion of the at least one of the pivot joints with respect to the delivery shaft.

For some applications, the fin includes a structural member and at least one substantially flow-resistant membrane member, which is securely mounted to at least a portion of the structural member, and the structural member is shaped so as to define the one or more pivot joints. For some applications, the fin includes a structural member and at least one substantially flow-resistant membrane member, which is securely mounted to at least a portion of the structural member, and the membrane member is shaped so as to define the one or more pivot joints.

For some applications, the portion of the delivery shaft has first and second ends from which respective first and second portions of the fin extend in a same radial direction from the longitudinal axis.

For some applications, the endovascular tool further includes a support structure, which is coupled to the delivery shaft, and the fin is coupled to the support structure, so as to be indirectly coupled to the delivery shaft.

For some applications, the endovascular tool includes exactly one fin.

For some applications, the fin is at least partially radiopaque. For some applications, the fin includes a structural member, and a plurality of radiopaque markers, which are fixed to the structural member, and which have a greater radiopacity per unit weight than that of the structural member.

For some applications, the fin includes a structural member and at least one substantially flow-resistant membrane member, which is securely mounted to at least a portion of the structural member. For some applications, the structural member includes a super-elastic material, such as a super-elastic metal alloy, e.g., Nitinol. For some applications, the flow-resistant membrane member includes an implantable-grade polymer, such as polytetrafluoroethylene (PTFE), e.g., expanded polytetrafluoroethylene (ePTFE). Alternatively, for some applications, the polymer includes a polyester. For some applications, the at least one membrane member has a surface area of between 9 and 50 mm2 when the fin is in its expanded state.

For some applications, a length of the delivery shaft is at least 10 times a greatest dimension of the fin measured in a direction parallel with the axis of rotation when the fin is in its expanded state.

For some applications, the fin has a substantially planar shape when in its expanded state. For example, the substantially planar shape may be selected from the group of shapes consisting of: a parallelogram, a rectangle, a square, a semicircle, a trapezoid, a shape defined by a curved segment having ends connected by a straight line, and a shape defined by an arc having ends connected by a straight line. For some applications, the fin has an airfoil shape when in its expanded state. For some applications, the fin is generally cylindrical when in its expanded state.

For some applications, the fin has a greatest length in a direction perpendicular to the axis of rotation, which greatest length is at least 200% greater when the fin is in its expanded state than when the fin is in its compressed state. For some applications, the fin has a greatest length in a direction perpendicular to the axis of rotation when the fin is in its expanded state, which greatest length is between 3 and 15 mm. For some applications, the fin has a greatest length in a direction perpendicular to the axis of rotation when the fin is in its compressed state, which greatest length is between 1.5 and 4 mm. For some applications, the fin is configured to assume the compressed state when constrained, and to assume the expanded state when relaxed. For some applications, an axial length of the fin along the axis of rotation is at least 50% greater when the fin is in its compressed state than when the fin is in its expanded state. For some applications, an axial length of the fin along the axis of rotation is between 6 and 20 mm when the fin is in its expanded state. For some applications, an axial length of the fin along the axis of rotation is between 10 and 40 mm when the fin is in its compressed state.

For any of the applications described above, the apparatus may further include a generally tubular outer shaft, in which the delivery shaft is at least partially positioned, and in which the fin is initially positioned in its compressed state at least partially alongside the delivery shaft. For some applications, the outer shaft, the delivery shaft, and the fin are configured such that longitudinal translation of the outer shaft with respect to the delivery shaft (a) in a first axial direction effects a transition of the fin from its compressed state to its expanded state, and (b) in a second axial direction opposite the first axial direction effects a transition of the fin from its expanded state to its compressed state. Alternatively, for some applications, the outer shaft, the delivery shaft, and the fin are configured such that rotation of the outer shaft with respect to the delivery shaft (a) in a first rotational direction effects a transition of the fin from its compressed state to its expanded state, and (b) in a second rotation direction opposite the first rotation direction effects a transition of the fin from its expanded state to its compressed state.

For any of the applications described above, the apparatus may further include an endovascular guidewire, and the delivery shaft is shaped so as to define a longitudinal bore therethrough, which is configured to allow deployment of the delivery shaft over the guidewire.

There is further provided, in accordance with an application of the present invention, a method including:

providing an endovascular tool including a longitudinal delivery shaft and a fin coupled to the delivery shaft;

endoluminally introducing the endovascular tool into one or more blood vessels of a subject while the fin is in a compressed state; and thereafter, transitioning the fin to an expanded state, in which state the fin is configured to pivot around an axis of rotation.

For some applications, the method further includes, after transitioning, generating a radiographic image of the fin using an imaging system. For some applications, the method further includes changing a spatial attitude of a component of the imaging system, responsively to the radiographic image, such that an image plane of the imaging system is generally parallel to a plane defined by the fin that is indicative of a direction of blood flow in a vicinity of the fin.

For some applications, the method further includes changing a spatial attitude of a component of the imaging system until an apparent shape of the fin, as shown in the radiographic image, no longer has a modified aspect ratio compared to its actual aspect ratio.

For some applications, the method further includes, after generating the image, assessing one or more apparent dimensions of the fin as shown in the image. For some applications, assessing includes assessing two or more apparent dimensions of the fin, and assessing at least one ratio between two of the two or more apparent dimensions. For some applications, the method further includes, after generating the image, assessing a reference dimension of a portion of the delivery shaft, and comparing the one or more apparent dimensions of the fin with the reference dimension. For some applications, assessing includes measuring the one or more apparent dimensions. For some applications, the method further includes, further including, after assessing, comparing the one or more apparent dimensions with one or more respective actual dimensions of the fin in its expanded state. For some applications, assessing includes assessing two or more apparent dimensions of the fin, and comparing includes comparing a ratio of two of the apparent dimensions with a ratio of two of the actual dimensions. For some applications, the method further includes changing a spatial attitude of a component of the imaging system responsively to the assessing. For some applications, changing includes changing the spatial attitude of the component such that an image plane of the imaging system is generally parallel to a plane defined by the fin that is indicative of a direction of blood flow in a vicinity of the fin. For some applications, assessing and changing the spatial attitude include repeatedly assessing and changing the spatial attitude until a desired relationship has been obtained between the apparent dimensions and the actual dimensions of the fin. For some applications, the imaging system is a fluoroscopy system, the component of the imaging system is a C-arm, and changing the spatial attitude includes changing the spatial attitude of the C-arm.

For some applications, the method further includes, after changing the spatial attitude:

withdrawing the endovascular tool;

introducing a medical device into vasculature of the subject; and orienting the medical device using one or more images generated by the imaging system.

For some applications, orienting include rotationally orienting the medical device.

For some applications, the medical device is a stent, and introducing and orienting includes introducing and orienting the stent. For some applications, the stent is shaped so as to define a lateral opening, and orienting the stent includes orienting the lateral opening. For some applications, orienting the lateral opening includes orienting the lateral opening to face in a direction that is parallel to the image plane. For some applications, the stent includes two or more radiopaque features distributed around the lateral opening, and orienting the lateral opening includes orienting the lateral opening such that at least a portion of the radiopaque features are aligned with one another in the one or more images.

For some applications:

the delivery shaft is shaped so as to define a longitudinal bore therethrough, endoluminally introducing the endovascular tool includes endoluminally introducing a guidewire into the one or more blood vessels, and advancing the delivery shaft over the guidewire such that the guidewire passes through the bore, withdrawing the endovascular tool includes leaving the guidewire in the one or more blood vessels, and introducing the medical device includes introducing the medical device over the guidewire.

For some applications, endoluminally introducing includes positioning the fin in a vicinity of a bifurcation between at least two blood vessels. For some applications, endoluminally introducing includes positioning the delivery shaft in the one or more blood vessels such that the fin is aligned with the bifurcation. For some applications, positioning the delivery shaft includes positioning two portions of the delivery shaft in left and right common iliac arteries, respectively.

For some applications, the method further includes identifying that the patient suffers from an aneurysm, and endoluminally introducing includes endoluminally introducing the endovascular tool responsively to the identifying.

For some applications, transitioning includes transitioning the fin to its expanded state in which the fin extends laterally from a portion of the delivery shaft, and a longitudinal axis of the portion coincides with the axis of rotation. For some applications, providing the endovascular tool includes providing the endovascular tool in which the fin is shaped so as to define one or more pivot joints, which rotatably couple the fin to the portion of the delivery shaft.

For some applications, providing the endovascular tool includes providing the endovascular tool further including a support structure, which is coupled to the delivery shaft, and the fin is coupled to the support structure, so as to be indirectly coupled to the delivery shaft.

For some applications, providing the endovascular tool includes providing the endovascular tool including exactly one fin.

For some applications, providing the endovascular tool includes providing the endovascular tool in which the fin is at least partially radiopaque.

For some applications, providing the endovascular tool includes providing the endovascular tool in which the fin includes a structural member and at least one substantially flow-resistant membrane member, which is securely mounted to at least a portion of the structural member.

For some applications, transitioning includes transitioning the fin to its expanded in which state the fin has a substantially planar shape. For example, the substantially planar shape may be selected from the group of shapes consisting of: a parallelogram, a rectangle, a square, a semicircle, a trapezoid, a shape defined by a curved segment having ends connected by a straight line, and a shape defined by an arc having ends connected by a straight line.

For some applications, providing the endovascular tool includes providing the endovascular tool further including a generally tubular outer shaft, and endoluminally introducing includes endoluminally introducing the outer shaft in which the delivery shaft is at least partially positioned, and in which the fin is initially positioned in its compressed state at least partially alongside the delivery shaft. For some applications, transitioning the fin to its expanded state includes longitudinally translating the outer shaft with respect to the delivery shaft in a first axial direction, and further including subsequently longitudinally translating the outer shaft with respect to the delivery shaft in a second axial direction opposite the first axial direction to effect a transition of the fin from its expanded state to its compressed state. Alternatively, for some applications, transitioning the fin to its expanded state includes rotating the outer shaft with respect to the delivery shaft in a first axial direction, and further including subsequently rotating the outer shaft with respect to the delivery shaft in a second axial direction opposite the first axial direction to effect a transition of the fin from its expanded state to its compressed state.

The present invention will be more fully understood from the following detailed description of embodiments thereof, taken together with the drawings, in which:

BRIEF DESCRIPTION OF THE DRAWINGS

FIGS. 1A-C are schematic illustrations of an endovascular tool in compressed, partially-expanded, and expanded states, respectively, in accordance with an application of the present invention;

FIGS. 2A-B are schematic illustrations of another configuration of the endovascular tool of FIGS. 1A-C in compressed and expanded states, respectively, in accordance with an application of the present invention;

FIGS. 10A-F are schematic illustrations of an exemplary transluminal procedure performed using the endovascular tool of FIGS. 1A-C, in accordance with an application of the present invention.

DETAILED DESCRIPTION OF APPLICATIONS

Figure 3:
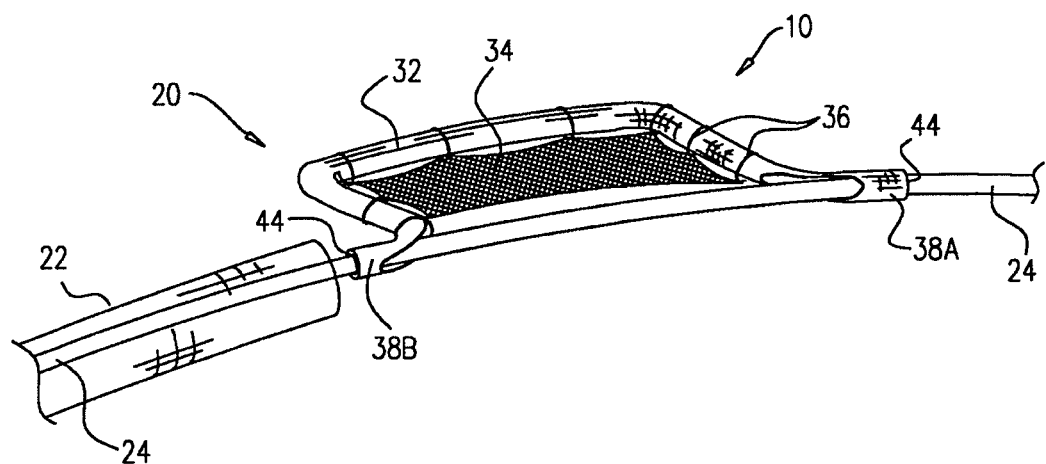
FIG. 3 is a schematic illustration of yet another configuration of the endovascular tool of FIGS. 1A-C in an expanded state, in accordance with an application of the present invention.

FIGS. 1A-C are schematic illustrations of an endovascular tool 10 in compressed, partially-expanded, and expanded states, respectively, in accordance with an application of the present invention. Endovascular tool 10 typically comprises a longitudinal delivery shaft 24 and a fin 20 coupled to the delivery shaft. The fin is configured to assume (a) a compressed state for endoluminal delivery (and, optionally, retrieval), as shown in FIG. 1A, and (b) an expanded state for endoluminal deployment, in which state the fin is configured to pivot around an axis of rotation 18, such as shown in FIG. 1C. Fin 20 typically assumes its compressed state when positioned a generally tubular outer shaft 22 at least partially alongside delivery shaft 24, initially before deployment of the fin, as described hereinbelow with reference to FIG. 10B, and, optionally, again subsequently to performing a calibration procedure using tool 10. FIG. 1B shows the fin in an intermediate, partially-expanded state, in which the fin is partially deployed from outer shaft 22. Typically, tool 10 comprises exactly one fin 20; alternatively, tool 10 comprises two or more fins (configuration not shown).

For some applications, fin 20 is relaxed in its expanded state. For some applications, the fin is configured to be self-expanding. For example, the fin may be heat-set to assume its expanded state. For some applications, fin 20 is configured to assume the compressed state when constrained (such as when within outer shaft 22), and to assume the expanded state when relaxed.

As described in more detail hereinbelow with reference to FIGS. 10C-D, fin 20 is configured such that, when the fin is placed in a blood flow path, at least a portion of the fin pivots in a direction that is indicative of the direction of blood flow in a vicinity of the fin.

Typically, fin 20 is pivotable to rotate at least 180 degrees around axis of rotation 18, as schematically indicated by an arrow 26 in FIG. 1C, at least when the fin is in its expanded state.

For some applications, fin 20 comprises a structural member 32 and at least one substantially flow-resistant membrane member 34, which is securely mounted to at least a portion of the structural member, either directly or indirectly, such as by a plurality of coupling elements 36, e.g., sutures or threads. For some applications, structural member 32 comprises a super-elastic material, such as a super-elastic metal alloy, e.g., Nitinol. Membrane member 34 typically comprises a thin pliable sheet of material, which may, for example, comprise an implantable-grade polymer, such as polytetrafluoroethylene (PTFE), e.g., expanded polytetrafluoroethylene (ePTFE), a polyester, or a textile material (e.g., polyethylene terephthalate (PET)). For some applications, membrane member 34 has a surface area of at least 9 mm2, no more than 50 mm2, and/or between 9 and 50 mm2.

For some applications, as shown in FIG. 1A-C (and FIGS. 2A-B, 3, 4, 5, 6, 8, 9A-C, and 10A-F, described hereinbelow), fin 20 extends laterally from a portion 28 of delivery shaft 24, and a longitudinal axis of portion 28 coincides with axis of rotation 18. For these applications, the longitudinal axis of portion 28 typically substantially lies within a plane 29 generally defined by fin 20 and/or membrane member 34 when the fin is in its expanded state, as shown in the side-view blow-up in FIG. 1C. Typically, portion 28 has first and second ends from which respective first and second portions of fin 20 extend in a same radial direction from longitudinal axis 18, for example, the direction indicated by a vector V in FIG. 1C. For other applications, such as described hereinbelow with reference to FIG. 7, axis of rotation 18 does not coincide with a longitudinal axis of delivery shaft 24.

Figure 8:
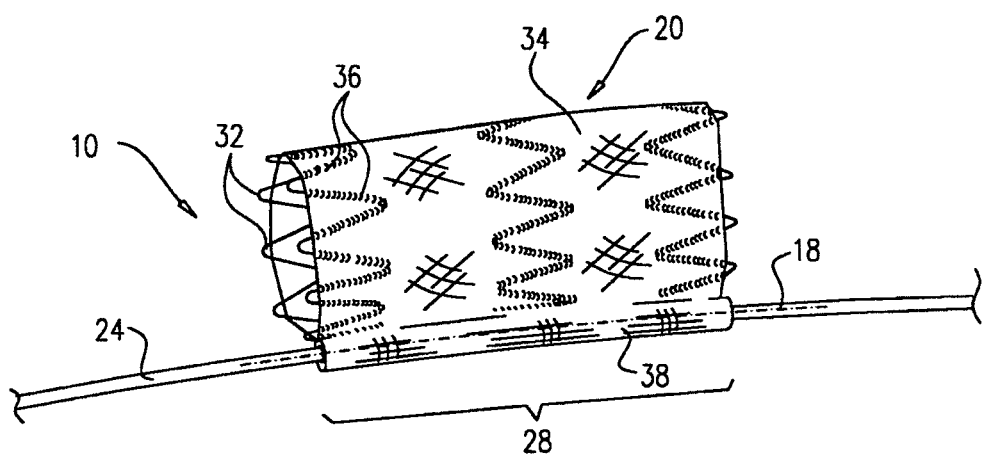
FIG. 8 is a schematic illustration of yet another configuration of the endovascular tool of FIGS. 1A-C in an expanded state, in accordance with an application of the present invention.

For some applications, fin 20 (typically, structural member 32 and/or membrane member 34) is shaped so as to define one or more pivot joints 38, which rotatably couple the fin to portion 28 of delivery shaft 24. For example, the pivot joints may include exactly two pivot joints 38A and 38B, such as shown in FIGS. 1A-C (and FIGS. 3-6, described hereinbelow). Alternatively, exactly one pivot joint may be provided, such as shown in FIG. 8, or more than two pivot joints may be provided, such as shown in FIGS. 2A-B, described hereinbelow. Typically, each of pivot joints 38 is shaped so as to surround at least 210 degrees of delivery shaft 24, such as at least 270 degrees, or 360 degrees (i.e., entirely surround the shaft), in order to be coupled to the delivery shaft. Typically, pivot joints 38 are configured to facilitate at least 180 degrees of rotation of the fin around the delivery shaft, as indicated by arrow 26 in FIG. 1C, at least when the fin is in its expanded state.

Typically, pivot joints 38 and delivery shaft 24 are configured to facilitate low-friction rotation of fin 20 around the delivery shaft, at least when the fin, is in its expanded state. For example, the pivot joints and the delivery shaft may be configured to provide a coefficient of static friction between the pivots and the delivery shaft of no more than 0.5, such as no more than 0.2. Alternatively or additionally, the pivot joints and the delivery shaft may be configured such that the pivot joints rotate with respect to the delivery shaft even when fin 20 is positioned in a blood flow of a healthy peripheral artery having a diameter of at least 3 mm in a subject having a systolic to diastolic blood pressure gradient of at least 30 mmHg.

For some applications, at least one (e.g., exactly one, or two or more) of pivot joints 38 is axially fixed to delivery shaft 24 so as to prevent axial motion of the at least one of the pivots with respect to the delivery shaft. Such fixation may aid in deployment of fin 20 from outer shaft 22, such as described hereinbelow with reference to FIG. 10C.

Figure 4:
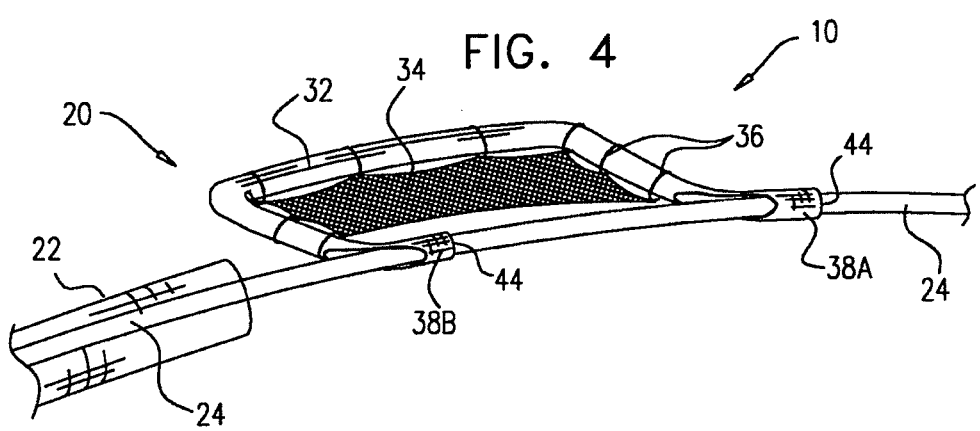
FIG. 4 is a schematic illustration of still another configuration of the endovascular tool of FIGS. 1A-C in an expanded state, in accordance with an application of the present invention.

For some applications, fin 20 has a substantially planar shape when in its expanded state. For example, the substantially planar shape may be a parallelogram, a rectangle (such as shown in FIGS. 2B, 3, and 4), a square, a semicircle, a trapezoid, a shape defined by a curved segment having ends connected by a straight line (such as shown FIGS. 1C and 6), or a shape defined by an arc having ends connected by a straight line.

For other applications, fin 20 has an airfoil shape (e.g., a symmetrical airfoil) when in its expanded state (configuration not shown). For still other applications, fin 20 is generally cylindrical when in its expanded state, such as described hereinbelow with reference to FIG. 8.

For some applications, a length of delivery shaft 24 is at least 10 times, such as at least 20 times a greatest dimension D1 of fin 20 measured in a direction parallel with axis of rotation 18, when the fin is in its expanded state, as shown in FIG. 1C. For some applications, greatest dimension D1 is at least 3 mm, no more than 30 mm, and/or between 3 and 30 mm. For some applications, a greatest dimension D2 of fin 20 measured in a direction parallel with axis of rotation 18, when the fin is in its compressed state, is at least 5 mm, no more than 50 mm, and/or between 5 and 50 mm, as shown in FIG. 1A. For some applications, delivery shaft 24 has a length of at least 10 cm, such as at least 50 cm.

For some applications, fin 20 has a greatest length L1 in a direction perpendicular to axis of rotation 24 when the fin is in its expanded state, which greatest length is at least 3 mm, no more than 15 mm, and/or between 3 and 15 mm, as shown in FIG. 1C. For some applications, fin 20 has a greatest length L2 in a direction perpendicular to axis of rotation 24 when the fin is in its compressed state, which greatest length is at least 1.5 mm, no more than 4 mm, and/or between 1.5 and 4 mm, as shown in FIG. 1A. For some applications, greatest length L1 (when the fin is in its expanded state) is at least 200% greater than greatest length L2 (when the fin is in its compressed state).

For some applications, an axial length L3 of fin 20 along axis of rotation 18 is at least 6 mm, no more than 20 mm, and/or between 6 and 20 mm when the fin is in its expanded state, as shown in FIG. 1C. (For some applications, greatest dimension D1 may be greater than axial length L3, when the greatest dimension does not coincide with axis of rotation 18.) For some applications, an axial length L4 of fin 20 along axis of rotation 18 is at least 10 mm, no more than 40 mm, and/or between 10 and 40 mm when the fin is in its compressed state, as shown in FIG. 1A. For some applications, axial length L4 (when the fin is in its compressed state) is at least 50% greater than axial length L3 (when the fin is in its expanded state).

For some applications, outer shaft 22, delivery shaft 24, and fin 20 are configured such that longitudinal translation of the outer shaft with respect to the delivery shaft (a) in a first axial direction (e.g., translation of the outer shaft to the left in FIGS. 1A-C) effects a transition of the fin from its compressed state (such shown in FIG. 1A) to its expanded state (such as shown in FIG. 1C), and (b) in a second axial direction opposite the first axial direction effects a transition of the fin from its expanded state to its compressed state. In other words, the fin is configured to be capable of being compressed by the outer shaft when withdrawn into the outer shaft.

For some applications, outer shaft 22, delivery shaft 24, and fin 20 are configured such that rotation of the outer shaft with respect to the delivery shaft (a) in a first rotational direction effects a transition of the fin from its compressed state to its expanded state, and (b) in a second rotation direction opposite the first rotation direction effects a transition of the fin from its expanded state to its compressed state. For example, outer shaft 22 and delivery shaft 24 may be shaped so as to define a threading therebetween.

For some applications, an endovascular guidewire 30 is provided. Delivery shaft 24 is shaped so as to define a longitudinal bore therethrough, which is configured to allow deployment of the delivery shaft over the guidewire.

Reference is now made to FIGS. 2A-B, which are schematic illustrations of another configuration of endovascular tool 10 in compressed and expanded states, respectively, in accordance with an application of the present invention. Except as described below, this configuration of tool 10 is generally similar to the configuration described hereinabove with reference to FIGS. 1A-C.

For some applications, as shown in FIGS. 2A-B, fin 20 (typically, structural member 32 and/or membrane member 34) is shaped so as to define three pivot joints 38, which rotatably couple the fin to portion 28 of delivery shaft 24. First and second ones of these pivot joints (38A and 38B) extend to respective axial ends of portion 28 of delivery shaft 24, and a third one of the pivot joints (38C) is positioned between first and second pivot joints 38A and 38B.

For some applications, as shown in FIGS. 2A-B, structural member 32 is shaped so as to define all three pivot joints 38A, 38B, and 38C. Optionally, pivot joint 38C is not directly coupled to the remainder of structural member 32. Typically, membrane member 34 is coupled to the portion of structural member 32 that defines pivot joint 38C (such as by coupling elements 36), as well as to the portion of structural member 32 that defines pivot joints 38A and 38B.

Although fin 20 is shown in FIG. 2B as having the shape of a rectangle when in its expanded state, the fin may alternatively have another shapes, such as the shapes described hereinabove with reference to FIGS. 1A-C, and/or shown in any of the other figures.

One or more of the features of the configuration of fin 20 described with referenced to and/or shown in FIGS. 2A-B may be implemented in combination with the features of fin 20 described with reference to and/or shown in FIGS. 1A-C, 3, 4, 5, 6, 7, 8, and/or 9A-C.

Reference is now made to FIG. 3, which is a schematic illustration of yet another configuration of endovascular tool 10 in an expanded state, in accordance with an application of the present invention. This configuration of tool 10 is generally similar to the configuration described hereinabove with reference to FIGS. 2A-B, except that fin 20 comprises only first and second pivot joints 38A and 38B, and not third pivot joint 38C. One or more of the features of the configuration of fin 20 described with referenced to and/or shown in FIG. 3 may be implemented in combination with the features of fin 20 described with reference to and/or shown in FIGS. 1A-C, 2A-B, 4, 5, 6, 7, 8, and/or 9A-C.

Reference is now made to FIG. 4, which is a schematic illustration of still another configuration of endovascular tool 10 in an expanded state, in accordance with an application of the present invention. Except as described hereinbelow with reference to FIGS. 1A-C and 2-7, this configuration of tool 10 is generally similar to the configuration described hereinabove with reference to FIG. 3.

One or more of the features of the configuration of fin 20 described with referenced to and/or shown in FIG. 4 may be implemented in combination with the features of fin 20 described with reference to and/or shown in FIGS. 1A-C, 2A-B, 3, 5, 6, 7, 8, and/or 9A-C.

Figure 5:
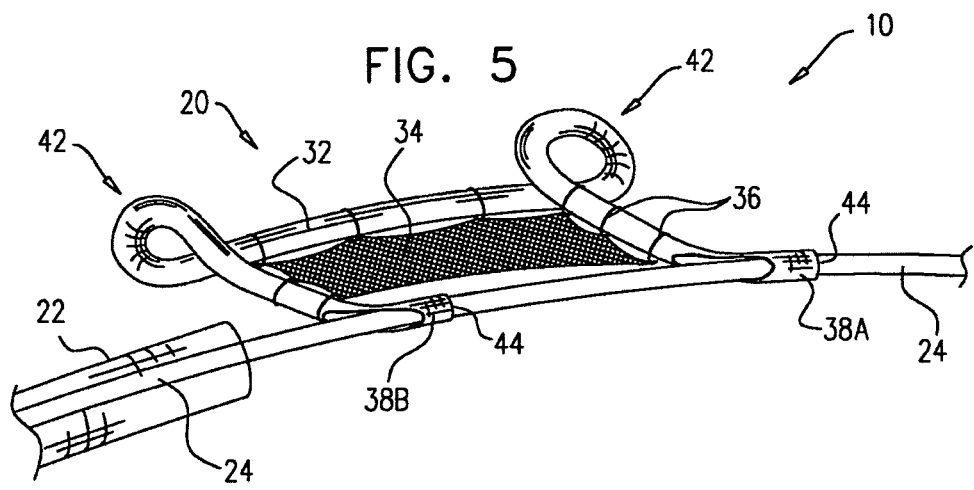
FIG. 5 is a schematic illustration of another configuration of the endovascular tool of FIGS. 1A-C in an expanded state, in accordance with an application of the present invention.

Reference is now made to FIG. 5, which is a schematic illustration of another configuration of endovascular tool 10 in an expanded state, in accordance with an application of the present invention. Except as described below, this configuration of tool 10 is generally similar to the configuration described hereinabove with reference to FIG. 4. In this configuration, structural member 32 is shaped so as to define one or more loops 42. These loops may serve to reduce kinking in at least one corner of the structural member, when the fin is folded into outer shaft 22.

One or more of the features of the configuration of fin 20 described with referenced to and/or shown in FIG. 5 may be implemented in combination with the features of fin 20 described with reference to and/or shown in FIGS. 1A-C, 2A-B, 3, 4, 6, 7, 8, and/or 9A-C.

Figure 6:
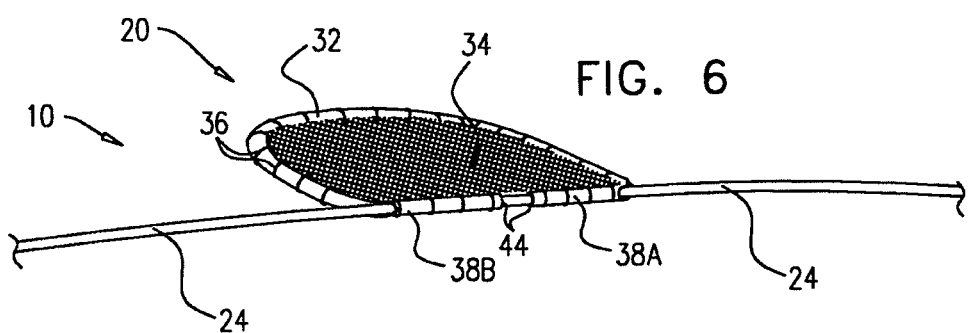
FIG. 6 is a schematic illustration of yet another configuration of the endovascular tool of FIGS. 1A-C in an expanded state, in accordance with an application of the present invention.

Reference is now made to FIG. 6, which is a schematic illustration of yet another configuration of endovascular tool 10 in an expanded state, in accordance with an application of the present invention. Except as described below, this configuration of tool 10 is generally similar to the configuration described hereinabove with reference to FIGS. 1A-C. In this configuration pivot joints 38A and 38B come nearly in contact with each other along delivery shaft 24 when the fin is in its expanded state, such as within 2 mm of each other.

One or more of the features of the configuration of fin 20 described with referenced to and/or shown in FIG. 6 may be implemented in combination with the features of fin 20 described with reference to and/or shown in FIGS. 1A-C, 2A-B, 3, 4, 5, 7, 8, and/or 9A-C.

Figure 7:
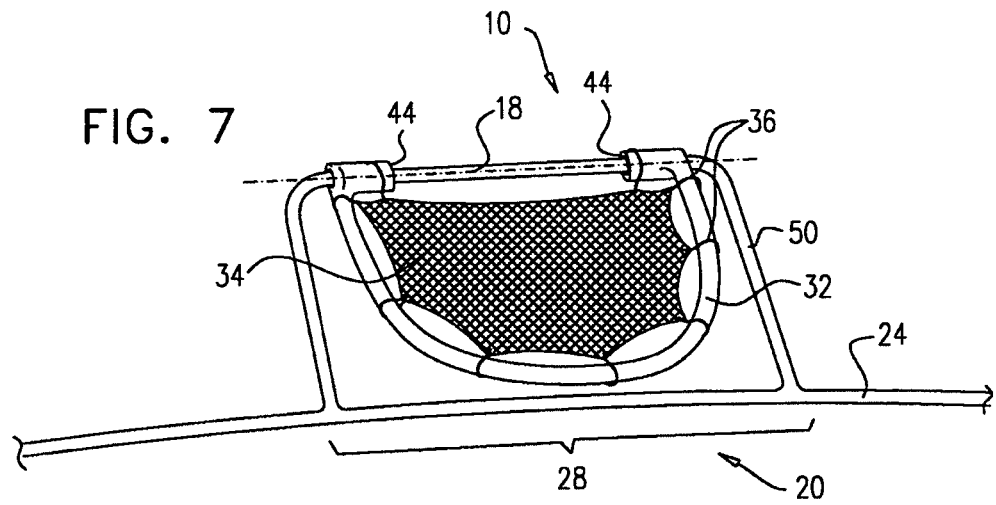
FIG. 7 is a schematic illustration of another configuration of the endovascular tool of FIGS. 1A-C in an expanded state, in accordance with an application of the present invention.

Reference is now made to FIG. 7, which is a schematic illustration of another configuration of endovascular tool 10 in an expanded state, in accordance with an application of the present invention. Except as described below, this configuration of tool 10 is generally similar to the configuration described hereinabove with reference to FIGS. 1A-C.

In this configuration, endovascular tool 10 further comprises a support structure 50, which is coupled to delivery shaft 24. For some applications, support structure 50 is rotationally fixed with respect to the delivery shaft and/or axially-fixed to the delivery shaft to prevent axial motion of the support structure with respect to the shaft. Alternatively, the support structure is only axially fixed to the shaft, only rotationally fixed to the shaft, or neither axially fixed nor rotationally fixed to the shaft. Fin 20 is coupled to support structure 50, so as to be indirectly coupled to delivery shaft 24. Fin 20 is configured to pivot around axis of rotation 18, which, in this configuration, does not coincide with the longitudinal axis of portion 28 of delivery shaft 24. For some applications, axis of rotation 18 coincides with an axis of a portion of support structure 50, such as shown in FIG. 7. For some applications, axis of rotation 18 is generally parallel with the longitudinal axis of portion 28 of delivery shaft 24, such as shown in FIG. 7. For other applications, the axis of rotation is not generally parallel with the longitudinal axis of portion 28 (configuration not shown).

One or more of the features of the configuration of fin 20 described with referenced to and/or shown in FIG. 7 may be implemented in combination with the features of fin 20 described with reference to and/or shown in FIGS. 1A-C, 2A-B, 3, 4, 5, 8, and/or 9A-C.

Reference is again made to FIGS. 1A-C and 2-7. For some applications, respective portions of structural member 32 that define pivot joints 38A and 38B have respective ends 44. For some applications, as shown in FIGS. 1A-C, 2A-B, 3, 6, and 7, ends 44 face in axially-opposite directions along axis of rotation 18. For some of these applications, such as shown in FIGS. 1A-C, 6, and 7, ends 44 face axially toward each other along axis of rotation 18, while for others of these applications, such as shown in FIGS. 2A-B and 3, ends 44 face axially away from each other along axis of rotation 18 (this configuration may facilitate retraction of the fin into outer shaft 22). For other applications, such as shown in FIGS. 4 and 5, ends 44 face in the same axial direction along axis of rotation 18.

Reference is now made to FIG. 8, which is a schematic illustration of yet another configuration of endovascular tool 10 in an expanded state, in accordance with an application of the present invention. In this configuration, fin 20 is generally cylindrical when in its expanded state. For some applications, a central axis of the fin 20 is generally parallel to axis of rotation 18, as shown in FIG. 8, while for other applications, the central axis of the fin is generally perpendicular to the axis of rotation (configuration not shown).

Figure 9A:
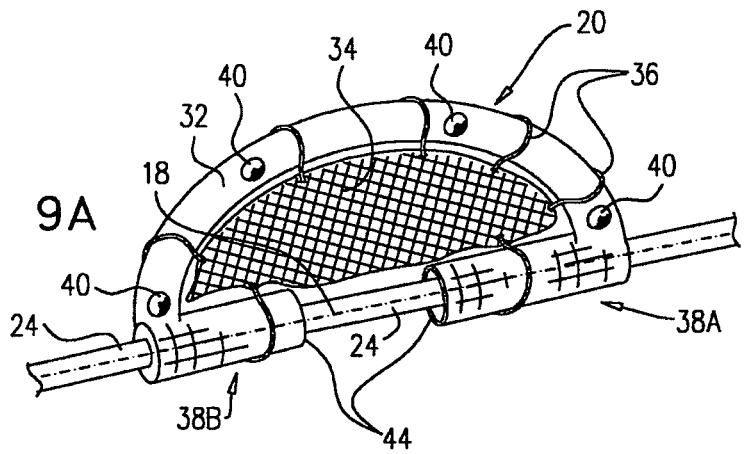
FIGS. 9A-C are schematic illustrations of respective configurations of the endovascular tool of FIGS. 1A-C in an expanded state, in accordance with respective applications of the present invention.
Figure 9B:
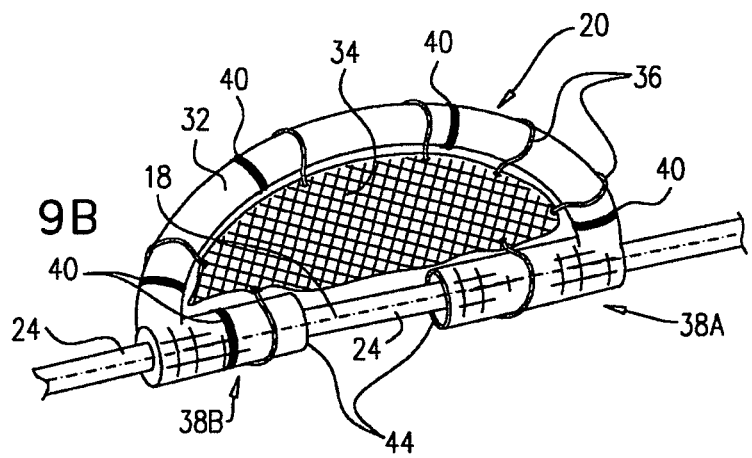
Figure 9C:
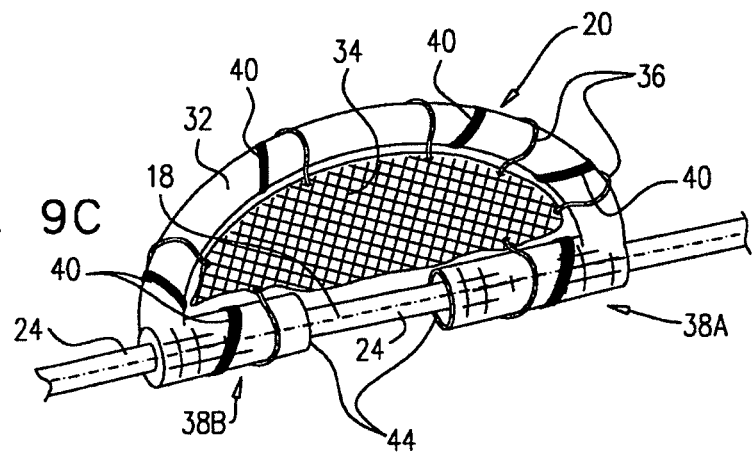

Reference is made to FIGS. 9A-C, which are schematic illustrations of respective configurations of endovascular tool 10 in an expanded state, in accordance with respective applications of the present invention. Typically, fin 20 is at least partially radiopaque, in order to facilitate radiographic imaging of the fin, such as described hereinbelow with reference to FIG. 10D. For some applications, fin 20 comprises a plurality of radiopaque markers 40, which are fixed to structural member 40, and have a greater radiopacity per unit weight than that of the structural member. For some applications, at least some of radiopaque markers 40 comprise small circular or semi-spherical elements, such as shown in FIG. 9A. Alternatively or additionally, at least some of radiopaque markers 40 comprise short tube segment, as shown in FIGS. 9B and 9C, which are wrapped around respective portions of structural member 32. Alternatively or additionally, some or all of radiopaque markers 40 are fixed to membrane member 34 (configuration not shown). Although FIGS. 9A-C illustrate radiopaque markers 40 applied to the configuration of fin 20 described hereinabove with reference to FIGS. 1A-C, the radiopaque markers may be similarly applied to the other configurations of fin 20 described herein, such as with reference to FIGS. 2A-B, 3, 4, 5, 6, 7, and/or 8.

Reference is now made to FIGS. 10A-F, which are schematic illustrations of an exemplary transluminal procedure performed using endovascular tool 10, in accordance with an application of the present invention. Although this procedure is illustrated using the configuration of tool 10 described hereinabove with reference to FIGS. 1A-C, the procedure may also be used to deploy the other configurations of tool 10 described herein, mutatis mutandis.

As shown in FIG. 10A, the exemplary procedures begins by endoluminally introducing guidewire 30 into one or more blood vessels of a subject. For example, fin 20 may be positioned in a vicinity of a bifurcation between at least two blood vessels, optionally aligned with the bifurcation, as shown in FIG. 10A. By way of example, in FIG. 10A the guidewire is shown introduced into left and right common iliac arteries 100A and 100B.

As shown in FIG. 10B, endovascular tool 10 is endoluminally introduced into the one or more blood vessels while fin 20 is in its compressed state. Typically, in order to endoluminally introduce the tool, delivery shaft 24 is passed over guidewire 30 such that the guidewire passes through a bore defined by the delivery shaft, and outer shaft 22 is also passed over the guidewire. Fin 20 is initially positioned in its compressed state within outer shaft 22, typically near a distal end of the outer shaft. Although delivery shaft 24 is shown by way of illustration in FIG. 10B as extending slightly distally out of the distal end of outer shaft 22, delivery shaft 24 does not necessarily extend out of outer shaft 22 at this stage of deployment.

Delivery shaft 24 and outer shaft 22 are longitudinally translated with respect to each other, thereby delivering fin 20 from the outer shaft, and transitioning fin 20 to its expanded state, as shown in FIG. 10C. For some applications, as shown, this relative longitudinal translation is effected by holding delivery shaft 24 in place as outer shaft 22 is withdrawn proximally. Alternatively, this relative longitudinal translation is effected by holding outer shaft 22 in place as delivery shaft 24 is advanced distally (technique not shown). As mentioned above with reference to FIGS. 1A-C, for some applications, at least one (e.g., exactly one, or two or more) of pivot joints 38 is axially fixed to delivery shaft 24 so as to prevent axial motion of the at least one of the pivots with respect to the delivery shaft. Such fixation may aid in deployment of the fin from outer shaft 22, by preventing fin 20 from moving with respect to outer shaft 22 as the delivery shaft and outer shaft are longitudinally translated with respect to each other.

In its expanded state, the fin is configured to pivot around the axis of rotation, as described hereinabove with reference to FIGS. 1A-C. When the fin is thus placed in a blood flow path (in this exemplary case, blood flow downstream from a descending abdominal aorta 102 into iliac arteries 100A and 100B), at least a portion of the fin pivots in a direction that is indicative of the direction of blood flow in the vicinity of the fin, as indicated by a vector V in FIG. 10C, perhaps best seen in Section A-A thereof. Tool 10 is positioned such that axis of rotation 18 (and, in the illustrated configuration, portion 28 of delivery shaft 24) is generally perpendicular to the direction of blood flow, in the vicinity of the axis of rotation.

As shown in FIG. 10D, a radiographic image (such as a fluoroscopy image) of fin 20 is generated using an imaging system 120 (such as a fluoroscopy imaging system). The image is used to align an image plane of imaging system 120 generally parallel to a plane 122 defined by the fin that is indicative of the direction of blood flow in the vicinity of the fin. Plane 122 is defined by (a) axis of rotation 18 (and, in the illustrated configuration, portion 28 of delivery shaft 24), and (b) vector V oriented in the direction that fin 20 extends from axis of rotation 18. (An "image plane," as used herein, including in the claims, is a plane that is perpendicular to the optical axis at any axial image point of the imaging system.)

In order to align the image plane of imaging system 120, a spatial attitude (i.e., an orientation or angular position) of a component of the imaging system (such as a C-arm 124) is changed (sometimes repeatedly), responsively to the radiographic image, until the image plane is generally parallel to plane 122.

For some applications, in order to align the image plane, after generating the image, one or more apparent dimensions of fin 20 as shown in the image are assessed, and the spatial attitude of the component of the imaging system is changed responsively to the assessing. In general, fin 20 (optionally, as represented by radiopaque markers 40) will appear distorted in the image to the extent that the image plane is not parallel with plane 122. The spatial attitude of the component of the imaging system is adjusted until fin 20 no longer appears distorted, indicating that the image plane and plane 122 are parallel. In other words, the spatial attitude of the component of the imaging system is adjusted until an apparent shape of the fin (either of the entire fin, or of a portion thereof, such as one or more radiographic markers thereof), as shown in the radiographic image, is no longer distorted compared to an actual shape of the fin, i.e., no longer has a modified aspect ratio compared to its actual aspect ratio. Typically, the assessing and changing of the spatial attitude are repeated until a desired relationship has been obtained between the apparent dimensions and the actual dimensions of the fin.

For example, two or more apparent dimensions of the fin may be assessed, and at least one ratio between two of the two or more apparent dimensions may be assessed. Alternatively or additionally, a reference dimension of a portion of the delivery shaft may be assessed, and the one or more apparent dimensions of the fin are compared with the reference dimension. In either case, the dimensions of the fin may include one or more of the following: one or more distances between respective sets of two features of the fin (e.g., radiopaque markers 40), a greatest width of the fin in a direction parallel with axis of rotation 24, and/or a greatest length of the fin in a direction perpendicular to axis of rotation 24.

For some applications, assessing comprises measuring the one or more apparent dimensions. For some applications, the one or more apparent dimensions are compared with one or more respective actual dimensions of the fin in its expanded state. For some applications, two or more apparent dimensions of the fin are assessed, and a ratio of two of the apparent dimensions are compared with a ratio of two of the actual dimensions.

After the imaging system has been properly aligned, delivery shaft 24 and fin 20 are withdrawn from the patient. Typically, fin 20 is first retracted into outer shaft 22, by either advancing outer shaft 22 distally, or withdrawing delivery shaft 24 proximally, until the fin reassumes its contracted state.

As shown in FIG. 10E, a medical device, such as a stent 106 (which, optionally, comprises a stent-graft), is introduced into vasculature of the subject, typically the one or more blood vessels from which the fin was withdrawn, or one or more other blood vessels in a vicinity of the one or more blood vessels from which the fin was withdrawn. The medical device is oriented using one or more images generated by the imaging system. Because the imaging system is properly aligned, as described above, the medical device can be properly aligned, for example, specifically in the rotational dimension, using images generated by the imaging system.

For some applications, the medical device, e.g., stent 106, is rotationally oriented using the one or more images generated by the imaging system. For example, the stent may be shaped so as to define a lateral opening 123, and the lateral opening may be rotationally oriented using the imaging system, such as to face in a direction that is parallel to the image plane. In the exemplary deployment procedure illustrated in FIGS. 10A-F, lateral opening 123 is oriented to face the opening between descending abdominal aorta 102 and left and right common iliac arteries 100A and 100B. If the imaging plane of imaging system 120 were not properly aligned as described above, the lateral opening would not be properly rotated to face the descending abdominal aorta, but instead would face another direction parallel to the misaligned imaging plane.

For some applications, stent 106 includes two or more radiopaque features 124 distributed around lateral opening 123. For some applications, lateral opening 123 is oriented such that at least a portion of radiopaque features 124 are aligned with one another in the one or more images. For example, as shown in FIG. 10E, stent 106 may be properly rotationally aligned when radiopaque feature 124A appears to coincide with radiopaque feature 124B in the two-dimensional radiographic image (because radiopaque feature 124A is directly above radiopaque feature 124B when viewed in the properly-aligned image plane), and radiopaque feature 124D appears to coincide with radiopaque feature 124C.

For some applications, the medical device, e.g., stent 106, is delivered in a radially-compressed state within a delivery shaft 130, as shown in FIG. 10E. The medical device is typically aligned while still compressed in the delivery shaft, which is generally readily rotated in the vasculature. Optionally, when delivery shaft 24 and fin 20 are withdrawn, as described above, guidewire 30 is left in the one or more blood vessels, and the medical device is introduced over the guidewire.

As shown in FIG. 10F, once properly aligned, the medical device, e.g., stent 106, is delivered from the delivery shaft, and transitions to a radially-expanded state. If necessary for precise alignment, the medical device typically can be further slightly rotated even after expansion thereof. For some applications, stent 106 may be configured using techniques described in US Patent Application Publication 2010/0063575, which is incorporated herein by reference, such as regarding stent graft component 60 thereof. For some applications, the techniques described herein are used for rotationally aligning stent graft component 60 of the '575 publication, optionally in combination with other apparatus and/or methods described in the '575 publication. For some applications, additional stents (e.g., stent-grafts) are deployed in combination with stent 106, either before or after deploying stent 106, such as using techniques described in one or more of the patent applications incorporated hereinbelow by reference.

For some applications of the present invention, a kit is provided that comprises endovascular tool 10 and at least one medical device, such as a stent (e.g., a stent-graft). For some applications, the kit further comprises delivery shaft 130 and/or guidewire 30.

For some applications, endovascular tool 10 is used to treat an aneurysm 104, such as an aortic aneurism, or an aneurism of another blood vessel. For example, the aneurism may be of the sub-renal aorta, as shown in FIGS. 10A-F. For some applications, a method is provided that comprises identifying that a patient suffers from an aneurysm, such as an aortic aneurism (e.g., a sub-renal aortic aneurism), and, responsively to the identifying, endoluminally introducing endovascular tool 10 responsively to the identifying, and, optionally, a medical device, such as a stent, e.g., a stent-graft. Techniques for identifying that a patient suffers from an aneurism are well known, and thus not described herein.

Although endovascular tool 10 has sometimes been described hereinabove as being deployed in the common iliac arteries in a vicinity of a bifurcation with the descending abdominal aorta, the endovascular tool may, for some applications, also be deployed in other body lumens, such as at other branching body lumens. For example, the tool may be deployed in the aortic arch in a vicinity of one of the branches of the aortic arch, and also when placing a fenestrated stent between the common carotid artery and either the internal or external carotid artery, and an additional stent between the fenestration of the aforementioned stent and the other carotid artery.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

PCT Application PCT/IL2008/000287, filed Mar. 5, 2008, which published as PCT Publication WO 2008/107885 to Shalev et al., and U.S. application Ser. No. 12/529,936 in the national stage thereof, which published as US Patent Application Publication 2010/0063575

U.S. application Ser. No. 12/529,936, which published as US Patent Application Publication 2010/0063575 to Shalev et al.

U.S. Provisional Application 60/892,885, filed Mar. 5, 2007

U.S. Provisional Application 60/991,726, filed Dec. 2, 2007

U.S. Provisional Application 61/219,758, filed Jun. 23, 2009

U.S. Provisional Application 61/221,074, filed Jun. 28, 2009

PCT Application PCT/IB2010/052861, filed Jun. 23, 2010, which published as PCT Publication WO 2010/150208

PCT Application PCT/IL2010/000564, filed Jul. 14, 2010, which published as PCT Publication WO 2011/007354

PCT Application PCT/IL2010/000917, filed Nov. 4, 2010, which published as PCT Publication WO 2011/055364

PCT Application PCT/IL2010/000999, filed Nov. 30, 2010, entitled, "Multi-component stent-graft system for implantation in a blood vessel with multiple branches," which published as PCT Publication WO 2011/064782

PCT Application PCT/IL2010/00101, filed Dec. 2, 2010, entitled, "Endovascular fenestrated stent-grafting," which published as PCT Publication WO 2011/067764

PCT Application PCT/IL2010/001037, filed Dec. 8, 2010, entitled, "Endovascular stent-graft system with fenestrated and crossing stent-grafts,"which published as PCT Publication WO 2011/070576

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising an endovascular tool, which comprises:
   a longitudinal delivery shaft; and
   a fin, which (1) is coupled to the delivery shaft, (2) comprises a structural member and at least one substantially flow-resistant membrane member, which is securely mounted to at least a portion of the structural member, and (3) which is configured to assume (a) a compressed state for endoluminal delivery, and (b) an expanded state for endoluminal deployment, in which state (i) the fin is configured to pivot around an axis of rotation that coincides with a longitudinal axis of a portion of the delivery shaft, (ii) the fin extends laterally from the portion of the delivery shaft, which portion has first and second ends, from which respective first and second portions of the structural member of the fin extend in a same radial direction from the longitudinal axis, and (iii) the fin has a substantially planar shape and extends in the same radial direction from the longitudinal axis,
   wherein the fin is shaped so as to define one or more pivot joints, which rotatably couple the fin to the portion of the delivery shaft, and
   wherein the delivery shaft is capable of rotating within the one or more pivot joints.

2. The apparatus according to claim 1, wherein the fin is configured such that, when the fin is placed in a blood flow path, at least a portion of the fin pivots in a direction that is indicative of a direction of blood flow in a vicinity of the fin.

3. The apparatus according to claim 1, wherein the endovascular tool further comprises a support structure, which is coupled to the delivery shaft, and wherein the fin is coupled to the support structure, so as to be indirectly coupled to the delivery shaft.

4. The apparatus according to claim 1, wherein the substantially flow-resistant membrane member comprises an implantable-grade polymer.

5. The apparatus according to claim 1, wherein a length of the delivery shaft is at least 10 times a greatest dimension of the fin measured in a direction parallel with the axis of rotation when the fin is in its expanded state.

6. The apparatus according to claim 1, further comprising a generally tubular outer shaft, in which the delivery shaft is at least partially positioned, and in which the fin is initially positioned in its compressed state at least partially alongside the delivery shaft.

7. The apparatus according to claim 6, wherein the fin is initially positioned in its compressed state near a distal end of the outer shaft, and wherein, when the fin is in its expanded state upon delivery through the distal end of the outer shaft, at least a portion of the one or more pivot joints is disposed distally to a proximal-most end of the fin.

8. The apparatus according to claim 1, wherein the fin is configured such that when the fin is placed in a blood flow path, the fin pivots such that the radial direction of the fin from the axis of rotation coincides with a direction of blood flow in a vicinity of the fin.

9. The apparatus according to claim 1, wherein the one or more pivot joints and the delivery shaft are configured to provide a coefficient of static friction between the one or more pivot joints and the delivery shaft of no more than 0.5.

10. The apparatus according to claim 1, wherein the one or more pivot joints and the delivery shaft are configured such that the one or more pivot joints rotate with respect to the delivery shaft even when the fin is positioned in a blood flow of a healthy peripheral artery having a diameter of at least 3 mm in a subject having a systolic to diastolic blood pressure gradient of at least 30 mmHg.

11. The apparatus according to claim 1, wherein the fin is pivotable to rotate at least 180 degrees around the axis of rotation, at least when the fin is in its expanded state.

12. The apparatus according to claim 1, wherein an element of the fin is shaped so as to define the one or more pivot joints, the element selected from the group consisting of: the structural member and the substantially flow-resistant membrane member.

13. The apparatus according to claim 1, wherein the fin is shaped so as to define two or more pivot joints, and wherein the delivery shaft is capable of rotating within the two or more pivot joints.

14. The apparatus according to claim 1, wherein at least one of the one or more pivot joints is axially fixed to the delivery shaft so as to prevent axial motion of the at least one of the one or more joints with respect to the delivery shaft.

15. The apparatus according to claim 14, wherein exactly one of the one or more pivot joints is axially fixed to the delivery shaft.

16. The apparatus according to claim 14, wherein two or more of the pivot joints are axially fixed to the delivery shaft.

17. Apparatus comprising an endovascular tool, which comprises:
a longitudinal delivery shaft; and
a fin, which is coupled to the delivery shaft, and which is configured to assume (a) a compressed state for endoluminal delivery, and (b) an expanded state for endoluminal deployment, in which state (i) the fin is configured to pivot around an axis of rotation, (ii) the fin extends laterally from a portion of the delivery shaft, (iii) a longitudinal axis of the portion coincides with the axis of rotation, and (iv) the fin has a planar shape,
wherein the fin is shaped so as to define one or more pivot joints, which rotatably couple the fin to the portion of the delivery shaft,
wherein the delivery shaft is capable of rotating within the one or more pivot joints, and
wherein the fin comprises a structural member and at least one substantially flow-resistant membrane member, which is securely mounted to at least a portion of the structural member.

18. Apparatus comprising an endovascular tool, which comprises:
a longitudinal delivery shaft; and
a fin, which is coupled to the delivery shaft, and which is configured to assume (a) a compressed state for endoluminal delivery, and (b) an expanded state for endoluminal deployment, in which state (i) the fin is configured to pivot around an axis of rotation, (ii) the fin extends laterally from a portion of the delivery shaft in exactly one radial direction, (iii) a longitudinal axis of the portion coincides with the axis of rotation, and (iv) the fin has a substantially planar shape,
wherein the fin is shaped so as to define one or more pivot joints, which rotatably couple the fin to the portion of the delivery shaft,
wherein the delivery shaft is capable of rotating within the one or more pivot joints, and
wherein the fin comprises a structural member and at least one substantially flow-resistant membrane member, which is securely mounted to at least a portion of the structural member.

19. A method comprising:
providing an endovascular tool including a longitudinal delivery shaft and a fin, which (a) is coupled to the delivery shaft, and (b) comprises a structural member and at least one substantially flow-resistant membrane member, which is securely mounted to at least a portion of the structural member;
endoluminally introducing the endovascular tool into one or more blood vessels of a subject while the fin is in a compressed state; and
thereafter, transitioning the fin to an expanded state, in which state (a) the fin is configured to pivot around an axis of rotation that coincides with a longitudinal axis of a portion of the delivery shaft, (b) the fin extends laterally from the portion of the delivery shaft, which portion has first and second ends, from which respective first and second portions of the structural member of the fin extend in a same radial direction from the longitudinal axis, and (c) the fin has a substantially planar shape and extends in the same radial direction from the longitudinal axis,
wherein the fin is shaped so as to define one or more pivot joints, which rotatably couple the fin to the portion of the delivery shaft, and
wherein the delivery shaft is capable of rotating within the one or more pivot joints.

20. The method according to claim 19, further comprising, after transitioning, generating a radiographic image of the fin using an imaging system.

21. The method according to claim 20, further comprising changing a spatial attitude of a component of the imaging system, responsively to the radiographic image, such that an image plane of the imaging system is generally parallel to a plane defined by the fin that is indicative of a direction of blood flow in a vicinity of the fin.

22. The method according to claim 20, further comprising changing a spatial attitude of a component of the imaging system until an apparent shape of the fin, as shown in the radiographic image, no longer has a modified aspect ratio compared to its actual aspect ratio.

23. The method according to claim 20, further comprising, after generating the image, assessing one or more apparent dimensions of the fin as shown in the image.

24. The method according to claim 23, wherein assessing comprises assessing two or more apparent dimensions of the fin, and assessing at least one ratio between two of the two or more apparent dimensions.

25. The method according to claim 23, further comprising, after generating the image, assessing a reference dimension of a portion of the delivery shaft, and comparing the one or more apparent dimensions of the fin with the reference dimension.

26. The method according to claim 23, further comprising, after assessing, comparing the one or more apparent dimensions with one or more respective actual dimensions of the fin in its expanded state.

27. The method according to claim 23, further comprising changing a spatial attitude of a component of the imaging system responsively to the assessing.

28. The method according to claim 27, wherein changing comprises changing the spatial attitude of the component such that an image plane of the imaging system is generally parallel to a plane defined by the fin that is indicative of a direction of blood flow in a vicinity of the fin. orienting the stent comprises orienting the lateral opening, and
wherein orienting the lateral opening comprises orienting the lateral opening to face in a direction that is parallel to the image plane.

29. The method according to claim 20, further comprising:
changing a spatial attitude of a component of the imaging system, responsively to the radiographic image; and
after changing the spatial attitude:
withdrawing the endovascular tool;
introducing a medical device into vasculature of the subject; and
orienting the medical device using one or more images generated by the imaging system.

30. The method according to claim 29,
wherein the medical device is a stent, and wherein introducing and orienting comprises introducing and orienting the stent,
wherein the stent is shaped so as to define a lateral opening, and wherein orienting the stent comprises orienting the lateral opening, and
wherein orienting the lateral opening comprises orienting the lateral opening to face in a direction that is parallel to the image plane.

31. The method according to claim 19, wherein endoluminally introducing comprises:
positioning the fin in a vicinity of a branching from a main blood vessel to two branching blood vessels, which main and branching blood vessels include the one or more blood vessels; and
positioning the delivery shaft in the one or more blood vessels such that the fin is aligned with the branching.

32. The method according to claim 19, wherein providing the endovascular tool comprises providing the endovascular tool further including a support structure, which is coupled to the delivery shaft, and wherein the fin is coupled to the support structure, so as to be indirectly coupled to the delivery shaft.

33. The method according to claim 19, wherein providing the endovascular tool comprises providing the endovascular tool further including a generally tubular outer shaft, and wherein endoluminally introducing comprises endoluminally introducing the outer shaft in which the delivery shaft is at least partially positioned, and in which the fin is initially positioned in its compressed state at least partially alongside the delivery shaft.

34. The method according to claim 33,
wherein endoluminally introducing comprises endoluminally introducing the outer shaft in which the fin is initially positioned in its compressed state near a distal end of the outer shaft, and delivering the fin through the distal end of the outer shaft, and
wherein transitioning comprises transitioning the fin to its expanded state, in which state at least a portion of the one or more pivot joints is disposed distally to a proximal-most end of the fin.

35. The method according to claim 19, wherein providing the endovascular tool comprises providing the fin configured such that when the fin is placed in a blood flow path of the one or more blood vessels, the fin pivots such that the radial direction of the fin from the axis of rotation coincides with a direction of blood flow in a vicinity of the fin.

36. The method according to claim 19, wherein providing the endovascular tool comprises providing the endovascular tool in which the one or more pivot joints and the delivery shaft are configured to provide a coefficient of static friction between the one or more pivot joints and the delivery shaft of no more than 0.5.

37. The method according to claim 19,
wherein the one or more blood vessels includes a healthy peripheral artery having a diameter of at least 3 mm,
wherein the subject has a systolic to diastolic blood pressure gradient of at least 30 mmHg, and
wherein transitioning comprises transitioning the fin to the expanded state, in which state the one or more pivot joints and the delivery shaft are configured such that the one or more pivot joints rotate with respect to the delivery shaft when the fin is positioned in a blood flow of the healthy peripheral artery.

38. The method according to claim 19, wherein providing the endovascular tool comprises providing the endovascular tool in which the fin is pivotable to rotate at least 180 degrees around the axis of rotation, at least when the fin is in its expanded state.

39. The method according to claim 19, wherein providing the endovascular tool comprises providing the endovascular tool in which an element of the fin is shaped so as to define the one or more pivot joints, the element selected from the group consisting of: the structural member and the substantially flow-resistant membrane member.

40. The method according to claim 19, further comprising, after transitioning the fin to the expanded state, ascertaining a direction of blood flow in a vicinity of the fin.

41. The method according to claim 19, wherein endoluminally introducing the endovascular tool comprises positioning the endovascular tool such that the axis of rotation is generally perpendicular to a direction of blood flow in a vicinity of the axis of rotation.

42. The method according to claim 19, wherein providing the endovascular tool comprises providing the endovascular tool in which the fin is shaped so as to define two or more pivot joints, and in which the delivery shaft is capable of rotating within the two or more pivot joints.

43. The method according to claim 19, wherein providing the endovascular tool comprises providing the endovascular tool in which at least one of the one or more pivot joints is axially fixed to the delivery shaft so as to prevent axial motion of the at least one of the one or more pivot joints with respect to the delivery shaft.

* * * * *